US009642746B2

(12) United States Patent
Berlin

(10) Patent No.: US 9,642,746 B2
(45) Date of Patent: *May 9, 2017

(54) GLAUCOMA SURGERY METHODS AND SYSTEMS

(71) Applicant: Michael Berlin, West Hollywood, CA (US)

(72) Inventor: Michael Berlin, West Hollywood, CA (US)

(*) Notice: Subject to any disclaimer, the term of this patent is extended or adjusted under 35 U.S.C. 154(b) by 453 days.

This patent is subject to a terminal disclaimer.

(21) Appl. No.: 14/191,277

(22) Filed: Feb. 26, 2014

(65) Prior Publication Data

US 2014/0288485 A1    Sep. 25, 2014

Related U.S. Application Data

(63) Continuation of application No. 11/874,179, filed on Oct. 17, 2007, now Pat. No. 8,679,089, which is a
(Continued)

(51) Int. Cl.
*A61F 9/007* (2006.01)
*A61F 9/008* (2006.01)
*A61F 9/00* (2006.01)

(52) U.S. Cl.
CPC ........ *A61F 9/00781* (2013.01); *A61F 9/0017* (2013.01); *A61F 9/00802* (2013.01);
(Continued)

(58) Field of Classification Search
CPC .............. A61F 9/00781; A61F 9/00802; A61F 9/00814; A61F 2009/00844;
(Continued)

(56) References Cited

U.S. PATENT DOCUMENTS 3,858,577 A    1/1975   Bass et al.
3,884,236 A *  5/1975   Krasnov ................. A61F 9/008
                                                          606/3
(Continued)

FOREIGN PATENT DOCUMENTS

DE    19840047 A1   3/2000
EP    0898947 A2    3/1999
(Continued)

OTHER PUBLICATIONS

Neuhann et al. "Excimer laser trabecular ablation ab interno (ELT) in the treatment of chronic open-angle glaucoma". Ophthalmo-Chirurgie 13: Offpring (2001)—provided by the Applicant in the U.S. Appl. No. 11/874,179.*
(Continued)

*Primary Examiner* — Kami A Bosworth
(74) *Attorney, Agent, or Firm* — Wilson, Sonsini, Goodrich & Rosati

(57) ABSTRACT

Methods and systems are disclosed for creating an aqueous flow pathway in the trabecular meshwork, juxtacanalicular trabecular meshwork and Schlemm's canal of an eye for reducing elevated intraocular pressure. Some embodiments described apparatus and methods useful in photoablation of tissues. In some embodiments, a photoablation apparatus is used to perforate a tissue, forming an aperture into a space behind the tissue. Gases formed during a photoablation process can be used to pressurize the space behind the tissue to enhance patency of the space. In some embodiments the tissue is the trabecular meshwork of the eye and a wall of Schlemm's canal, and the space behind the tissue is a portion of the lumen of Schlemm's canal. In some embodiments, the method is useful in the treatment of glaucoma by improving outflow from the anterior chamber of the eye into Schlemm's canal, reducing intraocular pressure.

21 Claims, 25 Drawing Sheets

Related U.S. Application Data continuation-in-part of application No. 09/860,842, filed on May 21, 2001.

(60) Provisional application No. 60/904,545, filed on Mar. 2, 2007, provisional application No. 60/852,549, filed on Oct. 17, 2006.

(52) U.S. Cl.
CPC .............. *A61F 2009/00844* (2013.01); *A61F 2009/00868* (2013.01); *A61F 2009/00891* (2013.01)

(58) Field of Classification Search
CPC   A61F 2009/00868; A61F 2009/00891; A61M 2210/0612
See application file for complete search history.

(56) References Cited

U.S. PATENT DOCUMENTS

| | | |
|---|---|---|
| 3,982,541 A | 9/1976 | L'Esperance, Jr. |
| 4,273,109 A | 6/1981 | Enderby |
| 4,391,275 A | 7/1983 | Fankhauser et al. |
| 4,461,294 A | 7/1984 | Baron |
| 4,470,407 A | 9/1984 | Hussein |
| 4,497,319 A | 2/1985 | Sekine et al. |
| 4,501,274 A | 2/1985 | Skjaerpe |
| 4,517,973 A | 5/1985 | Sunago et al. |
| 4,538,608 A | 9/1985 | L'Esperance, Jr. |
| 4,551,129 A | 11/1985 | Coleman et al. |
| 4,558,698 A | 12/1985 | O'Dell |
| 4,559,942 A | 12/1985 | Eisenberg |
| 4,580,559 A | 4/1986 | L'Esperance |
| 4,583,539 A | 4/1986 | Karlin et al. |
| 4,633,866 A | 1/1987 | Peyman et al. |
| 4,658,816 A | 4/1987 | Ector, Jr. |
| 4,660,546 A | 4/1987 | Herrick et al. |
| 4,671,273 A | 6/1987 | Lindsey |
| 4,722,350 A | 2/1988 | Armeniades et al. |
| 4,729,373 A | 3/1988 | Peyman |
| 4,770,654 A | 9/1988 | Rogers et al. |
| 4,791,927 A | 12/1988 | Menger |
| 4,846,172 A | 7/1989 | Berlin |
| 4,876,250 A | 10/1989 | Clark |
| 4,925,299 A | 5/1990 | Meisberger et al. |
| 4,994,060 A | 2/1991 | Rink et al. |
| 5,034,010 A | 7/1991 | Kittrell et al. |
| 5,092,837 A | 3/1992 | Ritch et al. |
| 5,123,902 A | 6/1992 | Muller et al. |
| 5,129,895 A | 7/1992 | Vassiliadis et al. |
| 5,254,112 A | 10/1993 | Sinofsky et al. |
| 5,273,056 A | 12/1993 | McLaughlin et al. |
| 5,300,020 A | 4/1994 | L'Esperance, Jr. |
| 5,359,685 A | 10/1994 | Waynant et al. |
| 5,360,399 A | 11/1994 | Stegmann |
| 5,371,078 A | 12/1994 | Clark et al. |
| 5,607,966 A | 3/1997 | Hellberg et al. |
| 5,643,250 A | 7/1997 | O'Donnell, Jr. |
| 5,657,760 A | 8/1997 | Ying et al. |
| 5,698,545 A | 12/1997 | Clark et al. |
| 5,704,907 A | 1/1998 | Nordquist et al. |
| 5,713,844 A | 2/1998 | Peyman |
| 5,722,970 A | 3/1998 | Colvard et al. |
| 5,736,491 A | 4/1998 | Patel et al. |
| 5,738,676 A | 4/1998 | Hammer et al. |
| 5,738,677 A | 4/1998 | Colvard et al. |
| 5,785,658 A | 7/1998 | Benaron et al. |
| 5,792,103 A | 8/1998 | Schwartz et al. |
| 5,811,453 A | 9/1998 | Yanni et al. |
| 5,865,831 A | 2/1999 | Cozean et al. |
| 5,885,279 A | 3/1999 | Bretton |
| 5,895,831 A | 4/1999 | Brasier et al. |
| 5,990,099 A | 11/1999 | Clark |
| 5,993,438 A | 11/1999 | Juhasz et al. |
| 5,997,531 A | 12/1999 | Loeb et al. |
| 6,002,480 A | 12/1999 | Izatt et al. |
| 6,059,772 A | 5/2000 | Hsia et al. |
| 6,083,193 A | 7/2000 | Kadziauskas et al. |
| 6,099,521 A | 8/2000 | Shadduck |
| 6,102,045 A | 8/2000 | Nordquist et al. |
| 6,146,375 A | 11/2000 | Juhasz et al. |
| 6,177,544 B1 | 1/2001 | Kanai et al. |
| 6,186,974 B1 | 2/2001 | Allan et al. |
| 6,251,103 B1 | 6/2001 | Berlin |
| 6,297,228 B1 | 10/2001 | Clark |
| 6,398,809 B1 | 6/2002 | Hoffmann et al. |
| 6,450,984 B1 | 9/2002 | Lynch et al. |
| 6,494,857 B1 | 12/2002 | Neuhann |
| 6,524,275 B1 | 2/2003 | Lynch et al. |
| 6,638,239 B1 | 10/2003 | Bergheim |
| 7,018,376 B2 | 3/2006 | Webb et al. |
| 7,125,119 B2 | 10/2006 | Farberov |
| 7,133,137 B2 | 11/2006 | Shimmick |
| 7,431,710 B2 | 10/2008 | Tu et al. |
| 8,123,729 B2 | 2/2012 | Yamamoto et al. |
| 8,540,659 B2 | 9/2013 | Berlin |
| 8,679,089 B2 | 3/2014 | Berlin |
| 2002/0013572 A1 | 1/2002 | Berlin |
| 2002/0072673 A1* | 6/2002 | Yamamoto ........... A61B 8/0841 600/452 |
| 2002/0082591 A1 | 6/2002 | Haefliger |
| 2002/0111608 A1 | 8/2002 | Baerveldt et al. |
| 2002/0165522 A1 | 11/2002 | Holmen et al. |
| 2003/0014092 A1 | 1/2003 | Neuhann |
| 2003/0105456 A1 | 6/2003 | Lin |
| 2003/0109907 A1 | 6/2003 | Shadduck |
| 2003/0175324 A1 | 9/2003 | Robinson et al. |
| 2003/0212387 A1 | 11/2003 | Kurtz et al. |
| 2003/0236483 A1 | 12/2003 | Ren |
| 2004/0070761 A1 | 4/2004 | Horvath et al. |
| 2004/0082939 A1 | 4/2004 | Berlin |
| 2004/0092856 A1 | 5/2004 | Dahan |
| 2004/0116909 A1 | 6/2004 | Neuberger et al. |
| 2004/0199149 A1 | 10/2004 | Myers et al. |
| 2004/0228013 A1 | 11/2004 | Goldstein et al. |
| 2005/0043722 A1 | 2/2005 | Lin |
| 2005/0165386 A1 | 7/2005 | Kurtz et al. |
| 2005/0240168 A1 | 10/2005 | Neuberger et al. |
| 2005/0245916 A1 | 11/2005 | Connor |
| 2005/0279369 A1 | 12/2005 | Lin |
| 2006/0021623 A1 | 2/2006 | Miller et al. |
| 2006/0050229 A1 | 3/2006 | Farberov |
| 2006/0084954 A1 | 4/2006 | Zadoyan et al. |
| 2006/0106370 A1 | 5/2006 | Baerveldt et al. |
| 2006/0114469 A1 | 6/2006 | Horvath et al. |
| 2006/0129141 A1 | 6/2006 | Lin |
| 2006/0155265 A1 | 7/2006 | Juhasz et al. |
| 2006/0195078 A1 | 8/2006 | Webb et al. |
| 2006/0200113 A1 | 9/2006 | Haffner et al. |
| 2006/0224146 A1 | 10/2006 | Lin |
| 2006/0259021 A1 | 11/2006 | Lin |
| 2007/0093794 A1 | 4/2007 | Wang et al. |
| 2007/0093796 A1 | 4/2007 | Raksi et al. |
| 2007/0121120 A1 | 5/2007 | Schachar |
| 2007/0173791 A1 | 7/2007 | Raksi |
| 2007/0208325 A1 | 9/2007 | Kurtz et al. |
| 2007/0219541 A1 | 9/2007 | Kurtz |
| 2007/0235543 A1 | 10/2007 | Zadoyan et al. |
| 2007/0236771 A1 | 10/2007 | Zadoyan et al. |
| 2008/0027519 A1 | 1/2008 | Guerrero |
| 2008/0058777 A1 | 3/2008 | Kurtz et al. |
| 2008/0082078 A1 | 4/2008 | Berlin |
| 2008/0082088 A1 | 4/2008 | Kurtz et al. |
| 2008/0091224 A1 | 4/2008 | Griffis, III et al. |
| 2008/0119827 A1 | 5/2008 | Kurtz et al. |
| 2008/0278687 A1 | 11/2008 | Somani |
| 2009/0118716 A1 | 5/2009 | Brownell |
| 2009/0118717 A1 | 5/2009 | Brownell et al. |
| 2009/0118718 A1 | 5/2009 | Raksi et al. |
| 2009/0131921 A1 | 5/2009 | Kurtz et al. |
| 2009/0137988 A1 | 5/2009 | Kurtz |
| 2009/0157062 A1 | 6/2009 | Hauger et al. |
| 2009/0171327 A1 | 7/2009 | Kurtz et al. |

(56) References Cited

U.S. PATENT DOCUMENTS

| | | | |
|---|---|---|---|
| 2009/0281530 A1 | 11/2009 | Korn | |
| 2010/0036488 A1 | 2/2010 | De Juan, Jr. et al. | |
| 2010/0324543 A1 | 12/2010 | Kurtz et al. | |
| 2011/0028948 A1 | 2/2011 | Raksi et al. | |
| 2011/0028949 A1 | 2/2011 | Raksi et al. | |
| 2011/0028950 A1 | 2/2011 | Raksi et al. | |
| 2011/0028951 A1 | 2/2011 | Raksi et al. | |
| 2011/0028952 A1 | 2/2011 | Raksi et al. | |
| 2011/0028953 A1 | 2/2011 | Raksi et al. | |
| 2011/0028954 A1 | 2/2011 | Raksi et al. | |
| 2011/0028955 A1 | 2/2011 | Raksi | |
| 2011/0028957 A1 | 2/2011 | Raksi et al. | |
| 2011/0028958 A1 | 2/2011 | Raksi et al. | |
| 2012/0283557 A1 | 11/2012 | Berlin | |
| 2014/0288485 A1 | 9/2014 | Berlin | |
| 2015/0080783 A1 | 3/2015 | Berlin | |
| 2015/0305939 A1 | 10/2015 | Vera, I et al. | |
| 2015/0305940 A1 | 10/2015 | Vera, I et al. | |
| 2015/0313759 A1 | 11/2015 | Vera, I et al. | |
| 2016/0095751 A1 | 4/2016 | Berlin | |

FOREIGN PATENT DOCUMENTS

| | | |
|---|---|---|
| WO | WO-9117793 A1 | 11/1991 |
| WO | WO-9620742 A1 | 7/1996 |
| WO | WO-9901063 A1 | 1/1999 |
| WO | WO-9945868 A1 | 9/1999 |
| WO | WO-0013627 A1 | 3/2000 |
| WO | WO-0067687 A1 | 11/2000 |
| WO | WO-0067687 A1 | 11/2000 |

OTHER PUBLICATIONS

Berlin, et al. Excimer laser photoablation in glaucoma filtering surgery. American journal of ophthalmology 103.5 (1987): 713.

Berlin, et al. Goniophotoablation: excimer laser glaucoma filtering surgery. Lasers Light Ophthalmol 2 (1988): 17-24.

Berlin, et al. Laser sclerostomy. The state of the art. Ophthalmol Clin North Am 6 (1993): 415-424.

Berlin, et al. Perspectives on new laser techniques in managing glaucoma. Ophthalmol Clin North Am 8 (1995): 341-363.

Berlin, M. Laser Therapy. In Becker-Shaffer's Diagnosis and Therapy of the Glaucomas. 1999:521-554.

Berlin M.D., M., "Photoablation—The Basis of Photochemical Laser Interactions," Ophthalmic Lasers: A Second Genreation, Edited by W. March M.D., 1990, pp. 85-91.

Berson, M.D., F.G., et al. "Obstruction of Aqueous Outflow by Sodium Hyaluronate in Enucleanted Human Eyes" American Journal of Ophthalmology, vol. 95, No. 5, 1983, pp. 668-672.

Brown M.D., R.H., et al. "Ab Interne Filtering Surgery Internal Sclerectomy with the Trabecuphine," Opthamology Clinics of North America, vol. 1, No. 2, Dec. 1988, pp. 199-207.

Cimberle, M. "Erbium Laser Cataract Surgery is Now Bimanual, Easier and Safer to Perform" Ocular Surgery News, Aug. 2000, 3 pages.

Co-pending U.S. Appl. No. 15/288,993, filed Oct. 7, 2016.

"Customized Ablation: The Wave Continues to Move Forward", Medical Laser Report, vol. 15, No. 12, Dec. 2001, pp. 4-5.

"Detector". Macmillan Online Dictionary.<http://www.macmillandictionary.com/dictionary/american/detector>.

"Detector". Oxford Dictionaries Online.< http://www.oxford-dictionaries.com/definition/detector>.

Dietlein, et al. Ab interno infrared laser trabecular ablation: preliminary short-term results in patients with open-angle glaucoma. Graefe's archive for clinical and experimental ophthalmology 235.6 (1997): 349-353.

Dietlein, et al. Erbium: YAG laser trabecular ablation (LTA) in the surgical treatment of glaucoma. Lasers in surgery and medicine 23.2 (1998): 104-110.

Dietlein et al; "Erbium:YAG Laser Ablation on Human Trabecular Meshwork by Contact Delivery Endoprobes"; Ophthalmic Surgery and Lasers; vol. 27, No. 11; Nov. 1996; pp. 939-945.

Dietlein, et al. Morphological variability of the trabecular meshwork in glaucoma patients: implications for non-perforating glaucoma surgery.British journal of ophthalmology 84.12 (2000): 1354-1359.

E. L'Esperance.Jr.. M.D.. "Ophthalmic Lasers Photocoagulation, Photoradiation. and Surgery," The C.V. Mosby Company, 1983 pp. 529-554.

"Sensor." Cambridge Advanced Learners Dictionary. Cambridge Dictionaries Online.<http://dictionary.cambridge.org/define.asp?dict=CALD&key=71811> .

"Sensor." Compact Oxford English Dictionary. AskOxford.com. <http://www.askoxford.com/concise_oed/sensor?view=uk>.

Fankhauser, et al. Optical principles related to optimizing sclerostomy procedures. Ophthalmic Surgery, Lasers and Imaging Retina 23.11 (1992): 752-761.

Final Office Action received for U.S. Appl. No. 09/860,842, mailed on Dec. 15, 2006, 8 pages.

Final Office Action received for U.S. Appl. No. 09/860,842, mailed on Dec. 30, 2009, 16 pages.

Final Office Action received for U.S. Appl. No. 09/860,842, mailed on Jan. 9, 2006 , 5 pages.

Final Office Action received for U.S. Appl. No. 09/860,842, mailed on Jul. 7, 2014, 16 pages.

Final Office Action received for U.S. Appl. No. 09/860,842, mailed on Nov. 24, 2008, 10 pages.

Final Office Action received for U.S. Appl. No. 10/640,464, mailed on Feb. 17, 2010, 12 pages.

Final Office Action received for U.S. Appl. No. 10/640,464, mailed on Jul. 17, 2014, 13 pages.

Final Office Action received for U.S. Appl. No. 10/640,464, mailed on Jul. 31, 2006, 7 pages.

Final Office Action received for U.S. Appl. No. 10/640,464, mailed on Nov. 24, 2008, 7 pages.

Final Office Action received for U.S. Appl. No. 10/640,464, mailed on Oct. 17, 2007 , 5 pages.

Final Office Action received for U.S. Appl. No. 11/874,179, mailed on Apr. 4, 2011, 24 pages.

Final Office Action received for U.S. Appl. No. 11/874,179, mailed on Jan. 14, 2010, 24 pages.

Final Office Action received for U.S. Appl. No. 11/970,488, mailed on Feb. 4, 2011, 10 pages.

Final Office Action received for U.S. Appl. No. 11/970,488, mailed on Oct. 16, 2009, 10 pages.

Hill, et al. Effects of pulse width on erbium: YAG laser photothermal trabecular ablation (LTA). Lasers in surgery and medicine 13.4 (1993): 440-446.

Hill, et al. Laser trabecular ablation (LTA). Lasers in surgery and medicine 11.4 (1991): 341-346.

Hoerauf, et al. Slit-lamp-adapted optical coherence tomography of the anterior segment. Graefe's archive for clinical and experimental ophthalmology 238.1 (2000): 8-18.

Huang, et al. Optical coherence tomography. Science (New York, NY) 254.5035 (1991): 1178-1181.

Iliev, et al. The repair response following Nd: YAG laser sclerostomy ab interno in rabbits. Experimental eye research 61.3 (1995): 311-321.

International preliminary examination report dated Sep. 19, 2002 for PCT Application No. PCT/US01/16317.

International search report dated Jul. 5, 2002 for PCT Application No. PCT/US01/16317.

Jacobi, et al. Microendoscopic trabecular surgery in glaucoma management. Ophthalmology 106.3 (1999): 538-544.

Jean et al "Noncontact photoacoustic spectroscopy during photoablation with a 193-nm excimer laser"; Ger J Ophthalmoi.;vol. 2, No. 6; Nov. 1993; pp. 404-408.

Jean et al. "Noncontact photoacoustic spectroscopy during photoablation with a 193-nm excimer laser" Ger. J. Ophthalmol.; vol. 2, No. 6; Nov. 1993; pp. 404-408.

(56) References Cited

OTHER PUBLICATIONS

Juhasz, et al. Application of Femtosecond Laser Surgery for the Treatment of Glaucoma; in Frontiers in Optics. OSA Technical Digest (CD) (Optical Society of America, 2008).
Larson M.D. et al., "Viscoelastic Agents", The CLAO Journal, vol. 15, No. 2, Apr. 1989, 10 pp.
Latina, et al. New Lasers for Glaucoma Surgery. In Principles and Practice of Ophthalmology. Elsevier Health Sciences. 2000:600-608.
Lee, et al. Short-pulsed neodymium-YAG laser trabeculotomy. An in vivo morphological study in the human eye. Investigative ophthalmology & visual science 29.11 (1988): 1698-1707.
Leitgeb, et al. Spectral measurement of absorption by spectroscopic frequency-domain optical coherence tomography. Optics letters 25.11 (2000): 820-822.
L'Esperance Jr. M.D., F., "Ophthalmic Lasers Photocoagulation, Photoradiation, and Surgery," The C.V. Mosby Company, 1983, pp. 529-538, 554.
Liesegang M.D., T., Viscoelastics, Interactions Opthalmology Clinics, vol. 33, No. 4, 1993, pp. 127-147.
Lin, C. Ph.D. Laser-Tissue Interactions. Ophthalmology Clinics of North America, vol. 6, No. 3, Sep. 1993. pp. 381-391.
M. Berlin M.D., "New Developments in Glaucoma Laser Surgery Procedures," Ophthalmology Clinics of North America. vol. II. No. 2. Jun. 1998. pp. 187-200.
M. Vogel, G. Scheurer, W. Neu, M. Dressel, H. Gerhardt, "Die Ablation des Trabekelwerks," Klin. Mbl. Augenheilk. 197 (1990) 250-253.
Martin Vogel, Kyra Lauritzen, "Punktuelle Excimerlaserablation des Trabekelwers Klinische Ergebnisse," Opthalmologe 1997 94:665-667.
M.Berlin M.D., "Coreneal Photoblation," Ophthalmic Lasers: A seceond Generation, Edited by March . M.d., 1990, pp. 93-104.
M.Berlin M.D., Excimer Laser Applications in Glaucona Surgery, Ophthalmology Clinics of North America, vol. 1, No. 2. Dec. 1988, pp. 255-263.
McHam, et al. Erbium: YAG laser trabecular ablation with a sapphire optical fiber. Experimental eye research 65.2 (1997): 151-155.
M.H. Vogel, P. Schildberg, "Histologische Friihergebnisse nach experimenteller Lasertrabekulopunktur," Klin. Mhl. Augenheilk. 163 (1973) 353-358.
MLase AG. Specifications ExTra—Laser for Glaucoma treatment. Jul. 13, 2012.
MLase AG. Specifications FIDO—Laser for ExTra Laser system. Jul. 13, 2012.
Muller, et al. Biophysics of the photoablation process. Lasers in Medical Science 6.3 (1991): 241-254.
Nakamura, et al. Femtosecond laser photodisruption of primate trabecular meshwork: an ex vivo study. Invest Ophthalmol Vis Sci. Mar. 2009;50(3):1198-204. doi: 10.1167/iovs.07-1536. Epub Oct. 3, 2008.
Neuhann, Th et al., "Excimer Laser Trabecular Ablation ab interne (EL T) in the Treatment of Chronic Open-Angle Glaucoma" Ophthalmo-Chirurgie 13: Offprint (2001).
Non-Final Office Action received for U.S. Appl. No. 09/860,842, mailed on Apr. 17, 2008, 10 pages.
Non-Final Office Action received for U.S. Appl. No. 09/860,842, mailed on Feb. 25, 2016, 21 pages.
Non-Final Office Action received for U.S. Appl. No. 09/860,842, mailed on Jun. 30, 2006, 5 pages.
Non-Final Office Action received for U.S. Appl. No. 10/640,464, mailed on Apr. 21, 2008, 7 pages.
Non-Final Office Action received for U.S. Appl. No. 10/640,464, mailed on Dec. 15, 2006, 8 pages.
Non-Final Office Action received for U.S. Appl. No. 10/640,464, mailed on Feb. 26, 2016, 27 pages.
Non-Final Office Action received for U.S. Appl. No. 10/640,464, mailed on Jun. 9, 2009, 11 pages.
Non-Final Office Action received for U.S. Appl. No. 10/640,464, mailed on Mar. 2, 2006, 5 pages.
Non-Final Office Action received for U.S. Appl. No. 11/874,179, mailed on Jul. 15 2010, 24 pages.
Non-Final Office Action received for U.S. Appl. No. 11/874,179, mailed on Jun. 26, 2009, 19 pages.
Non-Final Office Action received for U.S. Appl. No. 11/874,179, mailed on Mar. 7, 2013, 9 pages.
Non-Final Office Action received for U.S. Appl. No. 11/970,488, mailed on Feb. 27, 2009, 8 pages.
Non-Final Office Action received for U.S. Appl. No. 11/970,488, mailed on Jun. 19, 2012, 18 pages.
Non-Final Office Action received for U.S. Appl. No. 14/028,460, mailed on Jan. 12, 2016, 9 pages.
Notice of Allowance and Fee transmittal received for U.S. Appl. No. 11/970,488, mailed on May 3, 2013, 10 pages.
Notice of allowance dated Dec. 19, 2016 for U.S. Appl. No. 14/028,460.
Notice of Allowance received and Fee transmittal for U.S. Appl. No. 11/874,179, mailed on Oct. 30, 2013, 12 pages.
Notice of Allowance received for U.S. Appl. No. 11/970,488, mailed on Jun. 28, 2013, 6 pages.
Office Action dated Oct. 4, 2016 for U.S. Appl. No. 09/860,842.
Office action dated Oct. 6, 2016 for U.S. Appl. No. 10/640,464.
Office Action received for U.S. Appl. No. 09/860,842, mailed on Dec. 8, 2003 , 5 pages.
Office Action received for U.S. Appl. No. 09/860,842, mailed on Feb. 12, 2003 , 6 pages.
Olivius M.D., E., et al., "Interocular Pressure After Cataract Surgery with Healon," American Intraocular Implant Society, vol. 11, Sep. 1985, pp. 480-482.
Owen, David. A moving-mirror gonioscope for retinal surgery. 1977. British Journal of Ophthalmology, 61, 246-247.
Radhakrishnan, et al. Real-time optical coherence tomography of the anterior segment at 1310 nm. Archives of ophthalmology 119.8 (2001): 1179-1185.
Rosencwaig, A. "Photoacoustic spectroscopy." Annual review of biophysics and bioengineering 9.1 (1980): 31-54.
Royston, et al. Comparison of the thermal tissue effects produced by aged sapphire and silica hemispherical tips. Lasers in surgery and medicine 14.1 (1994): 47-58.
Shirato et al; "Internal Sclerostomy with Argon Contact Laser—Animal Experiment Using 5-Fiuorouracil"; Japanese Journal of Ophthalmol; 34(3); 1990; 381-387.
Shirato et al; "Internal Sclerostomy with Argon Contact Laser—Animal Experiment Using 5-Fiuorouracil"; Jpn J Ophthalmol; 34(3); 1990; 381-387 (Abstract).
Taboada, J. et al., "An Extreme Sensitivity in the Corneal Epithelium to FAR UV ArF Excimer Laser Pulses," Proc. of the Sci. Prog. of the Aerospace Med. Assoc., 1981, San Antonio, TX. pp. 98-99.
Toyran, et al. Femtosecond laser photodisruption of human trabecular meshwork: an in vitro study. Exp Eye Res. Sep. 2005;81(3):298-305.
Translated Article: Punktuelfe Excimerlaserablation des Trabekelwerks Klinische Ergebnisse (Punctual Excimer Laser Ablation of trabecular meshwork Clinical results) by Lauritzen and Vogel; Opthalmologe 1997 94:665-667.
Translation, "Showing translation for the ablation of the trabecular meshwork . . . " M. Vogel, G. Scheurer, W Neu, M. Dressel, H. Gerhardt; Klin. Mbl. Augenheilk. 197 (1990) 250-253.
Translation of M.H. Vogel, P. Schildberg, "[Histological findings afer experimental laser-trabecula-puncture {author's transl)]," Klin. Monbl Augenheilkd 1973, 163(3): 353-358.
Trokel M.D., S. et al., "Excimer Laser Surgery of the Cornea," American Journal of Ophthalmology, vol. 96, Dec. 1983, pp. 710-715.
Wolbarsht, M., "Laser Surgery: C02 or HF," Journal of Quantum Electronics, vol. QE20, No. 12, Dec. 1984, pp. 1427-1432.
Verdaasdonk, R.M., et al., "Ray Tracing of Optically Modified Fiber Tips 1: Spherical Probes," Applied Optics, vol. 30, No. 16, Jun. 1991, pp. 2159-2171.

(56) References Cited

OTHER PUBLICATIONS

Verdaasdonk, R.M., et al., "Ray Tracing of Optically Modified Fiber Tips 2: Laser Scalpels" Applied Optics, vol. 30, No. 16, Jun. 1991, pp. 2172-2177.

* cited by examiner

A

B

GLAUCOMA SURGERY METHODS AND SYSTEMS

RELATED APPLICATIONS

The present application is a continuation of U.S. application Ser. No. 11/874,179, filed Oct. 17, 2007, entitled "Glaucoma Surgery Methods and Systems", now U.S. Pat. No. 8,679,089, which claims the benefit of U.S. Provisional Application Ser. No. 60/852,549, filed Oct. 17, 2006, entitled "Pneumatic Tissueplasty" and claims the benefit of U.S. Provisional application Ser. No. 60/904,545, filed Mar. 2, 2007, entitled "Pneumatic Tissueplasty", U.S. application Ser. No. 11/874,179, filed Oct. 17, 2007, entitled "Glaucoma Surgery Methods and Systems", now U.S. Pat. No. 8,679, 089, is a continuation-in-part of U.S. application Ser. No. 09/860,842, filed May 21, 2001, entitled "Delivery System and Method of Use for the Eye;" the entire contents of all of the preceding applications are herein incorporated by reference in their entireties.

FIELD OF THE INVENTION

Embodiments described herein are related to devices and methods for treatment of human tissues, especially interior human tissue structures in the eye for restructuring, and more particularly for the treatment of glaucoma.

BACKGROUND OF THE INVENTIONS

Glaucoma, a serious long-term health care problem, is a disorder of the eye in which elevated intraocular pressure ultimately leads to damage to the optic nerve and eventually to blindness. Glaucoma has been cited as the second most common cause of blindness in the United States, affecting several million people.

In order to fully appreciate the described embodiments, a brief overview of the anatomy of the eye is provided. As schematically shown in FIG. 1, the outer layer of the eye includes a sclera 17 that serves as a supporting framework for the eye. The front of the sclera includes a cornea 15, a transparent tissue that enables light to enter the eye. An anterior chamber 7 is located between the cornea 15 and a crystalline lens 4. The anterior chamber 7 contains a constantly flowing clear fluid called aqueous humor 1. The crystalline lens 4 is connected to the eye by fiber zonules, which are connected to the ciliary body 3. In the anterior chamber 7, an iris 19 encircles the outer perimeter of the lens 4 and includes a pupil 5 at its center. The diameter of the pupil 5 controls the amount of light passing through the leu 4 to the retina 8. A posterior chamber 2 is located between the crystalline lens 4 and the retina 8.

As shown in FIG. 2, the anatomy of the eye further includes a trabecular meshwork 9, a narrow band of spongy tissue within the eye that encircles the iris 19. The trabecular meshwork varies in shape and is microscopic in size. It is generally triangular in cross-section, varying in thickness from about 100-200 nm. It is made up of different fibrous layers having micron-sized pores forming fluid pathways for the egress of aqueous humor from the anterior chamber. The trabecular meshwork 9 has been measured to about a thickness of about 100 μm at its anterior edge, Schwalbe's line 18, at the approximate juncture of the cornea 15 and sclera 17.

The trabecular meshwork widens to about 200 μm at its base where it and iris 19 attach to the scleral spur. The passageways through the pores in trabecular meshwork 9 lead through a very thin, porous tissue called the juxtacanalicular trabecular meshwork 13, which in turn abuts the interior side of a structure called Schlemm's canal 11. Schlemm's canal 11 is filled with a mixture of aqueous humor and blood components, and branches off into collector channels 12 that drain the aqueous humor into the venous system. Because aqueous humor is constantly produced by the eye, any obstruction in the trabecular meshwork, the juxtacanalicular trabecular meshwork, or Schlemm's canal, prevents the aqueous humor from readily escaping from the anterior eye chamber. This results in an elevation of intraocular pressure within the eye. Increased intraocular pressure can lead to damage of the optic nerve, and eventual blindness.

As shown in FIG. 2, the eye has a drainage system for the aqueous humor 1 located in the corneoscleral angle. In general, the ciliary body 3 produces the aqueous humor 1. This aqueous humor flows in a path from the posterior chamber 2 through the pupil 5 into the anterior chamber 7 to the trabecular meshwork 9 and into Schlemm's canal 11 to collector channels 12 to aqueous veins. The obstruction of the aqueous humor outflow, which occurs in most open angle glaucoma (i.e., glaucoma characterized by gonioscopically readily visible trabecular meshwork), is typically localized to the region of the juxtacanalicular trabecular meshwork 13, located between the trabecular meshwork 9 and Schlemm's canal 11, and, more specifically, the inner wall of Schlemm's canal.

When an obstruction develops, for example, at the juxtacanalicular trabecular meshwork 13, intraocular pressure gradually increases over time. Therefore, a goal of current glaucoma treatment methods is to prevent optic nerve damage by lowering or delaying the progressive elevation of intraocular pressure. Many have searched for an effective method of lowering and controlling intraocular pressure. In general, various pharmaceutical treatments have been employed to control intraocular pressure. While these treatments can be effective for a period of time, the intraocular pressure often continues to increase in many patients. The most frequent problems result from patients failing to follow their treatment regimen. As a result, inadequately controlled glaucoma leads to an increased risk of irreversible damage to the optic nerve, and ultimately, vision loss.

In current therapeutic approaches, after a trial of pharmaceutical treatments fails to stop the progression of elevated intraocular pressure, or in some cases as primary therapy, a surgical treatment method or procedure is generally performed on affected eyes. The human eye is a particularly challenging target for corrective surgery because of the size, fiagility, distribution and characteristics of interior tissues. Prior art surgical attempts to lower the intraocular pressure include various therapies that generally fall under the name "glaucoma filtering surgery."

The surgical therapies in current use, however, do not address the location of the outflow obstruction that is recognized for causing the elevated intraocular pressure. These procedures include mechanically cutting portions of the eye anatomy and are known by such names as trabeculectomy, trabeculotomy, goniotomy, and goniocurettage. Significantly, these techniques have been found to be unsuccessful for long term intraocular pressure control. In trabeculectomy, the most popular procedure in glaucoma surgery, an opening is created in the sclera to enable aqueous humor to drain into charmels external to the eye globe. This procedure, however, has many complications including leaks, infections, hypotony (e.g., low eye pressure), and requirements for post-operative needling, undesirable antimetabolite use, a need for flap suture adjustment to maintain the function of the opening, and a need for long-term monitoring to avoid late complications. Another procedure, deep sclerectomy, attempts to create an intrascleral filtration pocket, but does not alter anatomic relationships and does not treat the region of outflow obstruction. Another procedure, called viscocanalostomy, does attempt to alter the outflow obstruction between Schlemm's canal and the porous juxtacanalicular layer. In viscocanalostomy, an opening via the sclera is created in an attempt to localize and insert a tube into Schlemm's canal, without puncturing the trabecular meshwork. Schlenmm's canal is dilated by injection of viscoelastic materials into the canal. By altering the juxtacanalicular meshwork's anatomic relationships, an increased aqueous outflow results. Although the procedure attempts to address the outflow obstruction that causes the increased intraocular pressure, viscoanalostomy has not been successful in this regard. Thus, a new treatment method was needed for glaucoma that would be effective to address the outflow obstruction that is the proximate cause of elevated intraocular pressure.

In the prior art, lasers have been used to treat glaucoma. Specifically, lasers have been used to thermally modify and/or to puncture completely through various structures, including the trabecular meshwork, Schlemm's canal and the sclera. Moreover, lasers have been used in attempts to open the anterior chamber to an internal outflow rather than an external outflow channel, or reservoir. Early attempts utilized the lasers available at that time which included Q-switched ruby lasers, neodymium:yttrium:aluminum:garnet (Nd:YAG) lasers, and argon lasers.

These procedures have many names: laser trabeculopuncture, laseropuncture, goniopuncture, laser trabeculostomy, laser trabeculotomy, and laser trabeculoplexy. Each of the above described procedures attempted to remove or move or alter portions of the trabecular meshwork, but each suffer from certain limitations. First, in practice, they have limited ability to reduce the intraocular pressure to within a desirable range. Second, while most found initial success in creating a puncture through the meshwork, the short duration of the reduced intraocular pressure proved to be ineffective in treating the long term effects of glaucoma. As a result, patients required continual monitoring, and additional post operative procedures, to maintain lower intraocular pressure over extended time periods.

The short duration of the reduced pressure has been linked to the body's subsequent inflammatory healing response at the openings created in the eye. The trauma associated with the shearing and tearing of the tissues and the thermal tissue damage caused by the above procedures initiates wound-healing processes which tend, with time, to reseal the surgically created openings.

SUMMARY OF THE INVENTIONS

Early laser procedures failed for a number of reasons. These included, lack of consideration for the size of the openings in the trabecular meshwork, and the failure to recognize the importance of reducing collateral tissue damage surrounding the created hole. It has been seen that large areas of surrounding tissue damage invite greater inflammation that results in a greater healing response. In addition, if damage occurs to the outer wall of Schlemm's canal and collector channel openings, resultant scarring prevents aqueous humor egress through the distal outflow pathways and effectively eliminates any benefit of the attempted procedure. The actual and potential thermal effect produced by the lasers is a significant contributing factor to the resultant tissue damage.

The present disclosure is an improved glaucoma treatment by providing a method and delivery system for creating an aqueous outflow pathway through the trabecular meshwork, juxtacanalicular trabecular meshwork and Schlemm's canal of an eye in order to reduce elevated intraocular pressure. The method includes the steps of introducing a fiber-optic probe between the outer surface of the eye and the anterior chamber until a distal end of the fiber-optic probe is in contact with or adjacent to a target site including the trabecular meshwork, the juxtacanalicular trabecular meshwork and Schlemm's canal distal to the meshwork. Pulsed laser radiation is delivered from the distal end of the fiber-optic probe sufficient to cause photoablation of the juxtacanalicular trabecular meshwork and an inner wall of Schlemm's canal in the target tissues. The fiber-optic probe may be stationery or advanced creating an aperture through these tissues to enable and improve fluid flow from the anterior chamber of the eye. The pulsed radiation is delivered in wavelengths, pulse durations and fluences to cause a minimal thermal effect on the tissue while removing and modifying tissue.

In a second aspect of the disclosure, a method of controlling an interior anatomy of an eye during an intraocular procedure includes the steps of creating an opening in the eye, and filling the anterior chamber of the eye through the opening with a viscoelastic material. The interior pressure within the eye may be sensed with a pressure sensor. The interior pressure may be adjusted by controlling the amount of viscoelastic material so as to compress or decompress the interior anatomy of the eye at a predetermined target anatomy site. In one aspect, the interior anatomy includes the trabecular meshwork. Viscoelastic materials of various viscosities and other protective agents placed within structures enable micro-manipulation of such structures for surgical modification while protecting adjacent structures from possible damage. Schlemm's canal may be inflated to enable perforation of the inner wall while protecting the outer wall structures.

In a third aspect of the disclosure, a method of reducing intraocular pressure in an eye is provided by creating an aqueous flow pathway through the trabecular meshwork and the inner wall of Schlemm's canal in which an implant device is inserted into the aqueous flow pathway and serves as a conduit to remove aqueous humor. The implant device may extend from the anterior chamber of the eye or the trabecular meshwork to the inner wall or lumen of Schlemm's canal.

In a fourth aspect of the disclosure, an apparatus provides laser energy to target tissues of an eye. The apparatus includes a laser unit for generating laser energy, and a delivery system that includes a laser probe. The laser probe includes an optical fiber core for transmitting laser energy from a distal end to target tissues of the eye, and a proximal end for coupling to the laser unit and may include sensing devices which generate and receive signals to enable a controller. In some embodiments, the sensing device features a sensor for sensing the temperature in the eye and at the target tissues before, during and after photoablation of the target tissues. In some embodiments, the sensing device has a sensor for sensing the laser probe relationship to the target tissues. In some embodiments, the sensing device has a sensor for sensing the pressure both within the eye and at the probe/target tissues. A servo feedback mechanism may utilize sensed pressure to provide a controlled adjustment of the treatment parameters.

In a fifth aspect of the disclosure, a device for reducing and maintaining reduced intraocular pressure is implanted into at least an inner wall of Schlemm's canal or adjacent trabecular meshwork. The device may include a tubular portion having a distal end including a first engaging member for attaching to the interior surface of the proximal inner wall of Schlemm's canal or adjacent trabecular meshwork. The tubular portion includes a proximal end having a plurality of second engaging members for attaching to the trabecular meshwork.

Some embodiments describe a method, of treating glaucoma in an eye, including creating an aperture through a first layer of eye tissue at a target site located in an anterior portion of the eye; advancing a distal portion of a delivery device through the first layer of eye tissue to a location between the first layer of eye tissue and a second layer of eye tissue, the location being within a space between the first layer and second layer of eye tissue, a distal opening of the delivery device being in fluid communication with the space between the first and second layers of eye tissue; advancing, through the distal portion of the delivery device, a fluid comprising an angiostatic steroid toward the distal opening of the delivery device; and administering, through the distal opening of the delivery device, the fluid into the space between the first and second layers of eye tissue; wherein the administering of the fluid expands the space between the first and second layers of eye tissue as the first layer of eye tissue is further separated from the second layer of eye tissue by deposition of the fluid in the space; and wherein the administering of the fluid is adapted to result in a lowered intraocular pressure in the eye.

In some embodiments, the space comprises a natural space. In some embodiments, the lowered intraocular pressure is achieved by keeping the aperture open. In some embodiments, the eye tissue comprises trabecular meshwork. In some embodiments, the eye tissue comprises a wall of Schlemm's canal. In some embodiments, the lowered intraocular pressure is achieved by a pharmacological effect of the angiostatic steroid. In some embodiments, the pharmacological effect comprises an anti-inflammatory effect. In some embodiments, the lowered intraocular pressure is achieved by keeping an aperture in eye tissue open by a pharmacologic action of the angiostatic steroid. In some embodiments, the angiostatic steroid comprises anecortave acetate. In some embodiments, the fluid comprises a viscoelastic fluid. In some embodiments, the fluid comprises molecules having a molecular size that is larger than a pore size of the first layer of eye tissue. In some embodiments, the aperture comprises cutting the first layer of eye tissue with a cutting device. In some embodiments, the fluid flows through the delivery device under positive pressure. In some embodiments, the fluid is advanced through a fluid pathway coaxial with the delivery device.

In some embodiments, the methods further include advancing the distal portion of the delivery device through the anterior chamber of the eye toward the trabecular meshwork and creating the aperture in the trabecular meshwork. In some embodiments, the first layer of eye tissue comprises the trabecular meshwork, the second layer of tissue comprises a portion of an outer wall of Schlemm's canal, and the space comprises a portion of a lumen of Schlemm's canal.

Some embodiments herein describe a method, of treating glaucoma in an eye, including creating an aperture through a first layer of eye tissue at a target site located in an anterior portion of the eye; advancing a distal portion of a delivery device through the first layer of eye tissue to a location between the first layer of eye tissue and a second layer of eye tissue, the location being within a space between the first layer and second layer of eye tissue, a distal opening of the delivery device being in fluid communication with the space between the first and second layers of eye tissue; advancing, through the distal portion of the delivery device, a fluid comprising an angiostatic steroid toward the distal opening of the delivery device; and administering, through the distal opening of the delivery device, the fluid into the space between the first and second layers of eye tissue; wherein the administering of the fluid expands the space between the first and second layers of eye tissue as the first layer of eye tissue is thinned by deposition of the fluid in the space; wherein the administering of the fluid is adapted to result in a reduced intraocular pressure in the eye.

Some embodiments describe a method, of guiding a glaucoma surgery, including advancing a distal portion of a treatment device, the treatment device having a hemoglobin detector, through an anterior chamber of an eye to a location adjacent Schlemm's canal of the eye; and detecting, with the hemoglobin detector, a presence of blood in Schlemm's canal.

In some embodiments, the presence of blood is detected with optical spectroscopy. Some embodiments further include identifying a location of Schlemm's canal based on the presence of the blood in Schlemm's canal and creating an aperture in the trabecular meshwork of the eye adjacent to the location of the blood.

Some embodiments described herein include a method, of performing glaucoma surgery, including advancing a distal portion of a treatment device through an anterior chamber of an eye to a location adjacent Schlemm's canal of the eye; penetrating an inner wall of Schlemm's canal with a distal end of the treatment device; and detecting penetration of the inner wall of Schlemm's canal with at least one of chemical detection, photochemical detection, hemoglobin detection, optical spectroscopy, detection of a fluorescent substance, and photoacoustic spectroscopy.

Some embodiments described herein include a method, of treating glaucoma of an eye, including advancing a distal portion of a treatment device through an anterior chamber of an eye; identifying an anatomical landmark in said eye; positioning the distal portion of the treatment device at a location with respect to the anatomical landmark; and creating an aperture in the trabecular meshwork of the eye, the aperture extending through the trabecular meshwork and providing fluid communication between an anterior chamber of the eye and Schlemm's canal of the eye. In some embodiments, the anatomical landmark is Schwalbe's line.

Some embodiments describe an apparatus, for treating glaucoma of an eye, including a laser that is configured to produce a beam that ablates a region of a trabecular meshwork of the eye; and a delivery system that is configured to direct the beam from within the eye to the trabecular meshwork of the eye, said delivery system being further configured to direct a gas bubble in the eye through the trabecular meshwork and into Schlemm's canal of the eye.

Some embodiments further include a sensor coupled to the delivery system, the sensor being configured to detect contact of a portion of the apparatus with a surface of the trabecular meshwork. In some embodiments, the delivery system comprises a hood that is configured to direct the gas bubble through the trabecular meshwork. Some embodiments further include a gas injector module, said gas injector module configured to inject a gas from outside the eye into an aperture formed in the trabecular meshwork and into Schlemm's canal. Some embodiments further include a sensor module that is configured to detect patency of an aperture formed in the trabecular meshwork. In some embodiments, the sensor module is configured to detect a gas bubble that moves from Schlemm's canal through the aperture.

Some embodiments herein describe an apparatus, for treating glaucoma of an eye, including a laser device that is configured to deliver laser light that ablates trabecular meshwork tissue of an eye to create an aperture in the trabecular meshwork; and a contact sensor that detects contact of the apparatus with the trabecular meshwork; wherein the laser device directs cavitation bubbles through the aperture in the trabecular meshwork into Schlemm's canal.

Some embodiments herein describe a method, for treating glaucoma of an eye, including creating an aperture in eye tissue; forming a gas bubble within the eye by ablation of eye tissue; and directing the gas bubble from within the anterior chamber through the aperture and into a natural aqueous outflow pathway of the eye, thereby modifying the natural aqueous outflow pathway. In some embodiments, the natural aqueous outflow pathway comprises at least one of Schlemm's canal, collector channels, and an episcleral vein of the eye.

Some embodiments describe a method including photoablating a tissue of an eye at a first treatment site, resulting in the formation of a first aperture in the eye tissue; photoablating the eye tissue at a second treatment site, resulting in the formation of a second aperture in the eye tissue; and forming a gas bubble within the eye by ablation of eye tissue; directing the gas bubble from within the anterior chamber of the eye through the first aperture and into a natural aqueous outflow pathway of the eye; and detecting the presence of the gas bubble after the gas bubble moves through the natural aqueous outflow pathway through the second aperture and into the anterior chamber. In some embodiments, the eye tissue comprises a trabecular meshwork of the eye, and the natural aqueous outflow pathway comprises Schlemm's canal of the eye.

In some embodiments, a method, of treating glaucoma, includes providing a volume of gas that comprises a therapeutic agent; and directing the volume of gas into an eye to alter, move, or separate structures within the eye.

BRIEF DESCRIPTION OF THE DRAWINGS

The foregoing summary of this disclosure, as well as the following detailed description of the preferred embodiments is further understood when read in conjunction with the accompanying drawings, which are included by way of example, and not by way of limitation with regard to this disclosure.

DETAILED DESCRIPTION OF THE INVENTIONS

Figure 3:
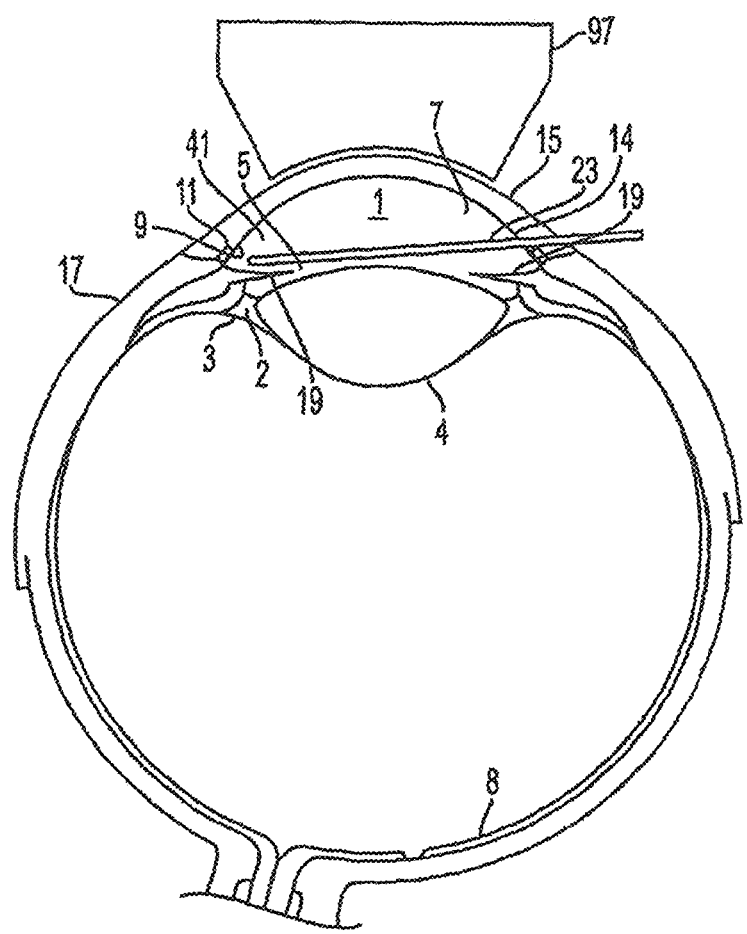
FIG. 3 is schematic sectional view of an eye illustrating a fiber-optic probe disposed next to the trabecular meshwork in the anterior chamber of the eye.
Figure 4:
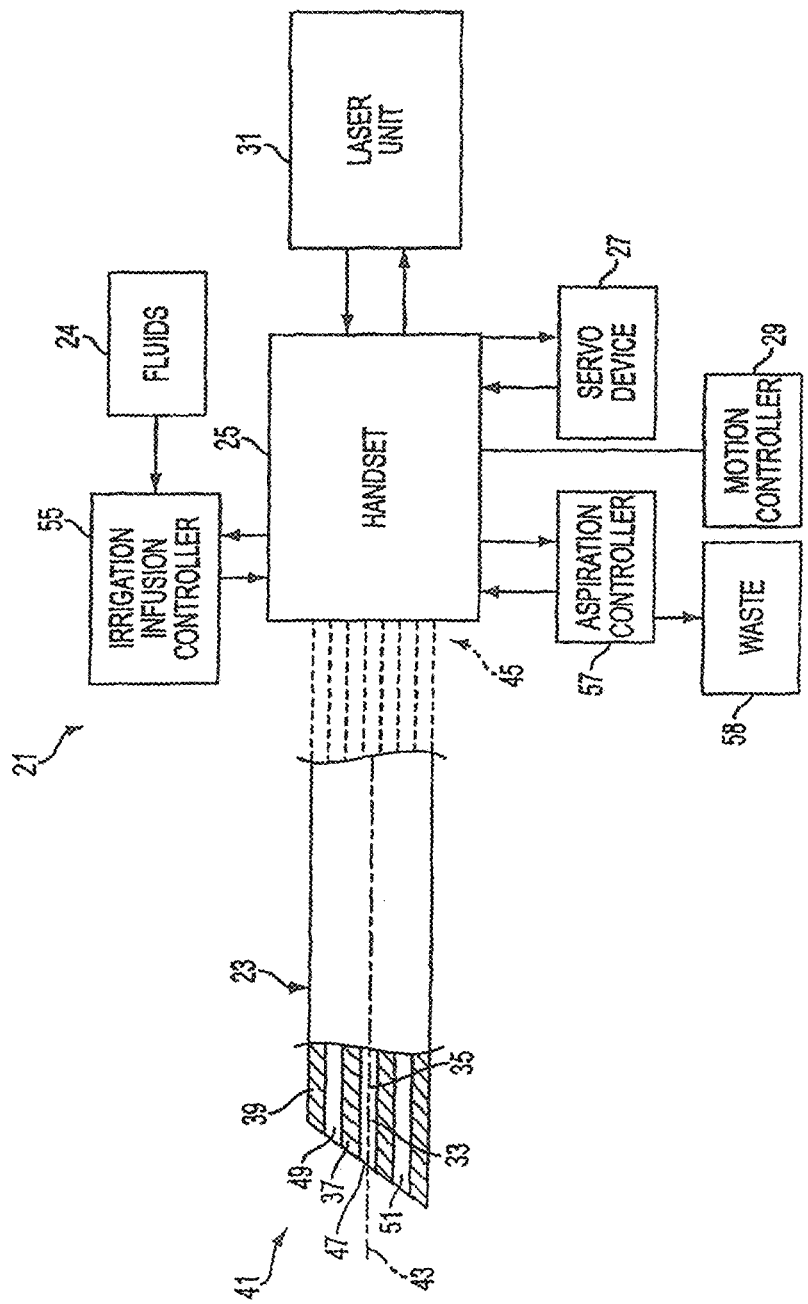
FIG. 4 is a schematic diagram of an embodiment of a laser delivery system including a side-sectional fragmentary view of the operative end of a fiber-optic probe.

FIGS. 3-12 illustrate an embodiment of a laser delivery system 21 for micromachining, microsculpting, or microshaping, the interior anatomy of an eye. As shown in FIG. 4, a laser delivery system 21 can be operated to reduce the thermal component of laser energy contributing to collateral tissue damage. As further shown in FIG. 4, laser delivery system 21 can include a fiber-optic probe 23 for entering the eye and removal or manipulation of eye tissue. In some embodiments, a fiber-optic probe 23 is mechanically and electrically coupled to a probe handset 25. Probe handset 25 includes controls for manipulating and operating the fiber-optic probe. A servo device 27 is connected to fiber-optic probe 23 for automatically controlling pressure within the eye during an intraocular procedure. In some embodiments, a motion controller 29 can selectively automate transocular movement of fiber-optic probe 23 to a site for tissue removal and/or manipulation. A laser unit 31 provides laser energy in the form of wavelength pulses through fiber-optic probe 23 for tissue removal from the interior of the eye by photoablation. Photoablation is the process of removing surface tissues, typically via laser energy, with minimal thermal transfer to the surrounding tissues.

Figure 13:
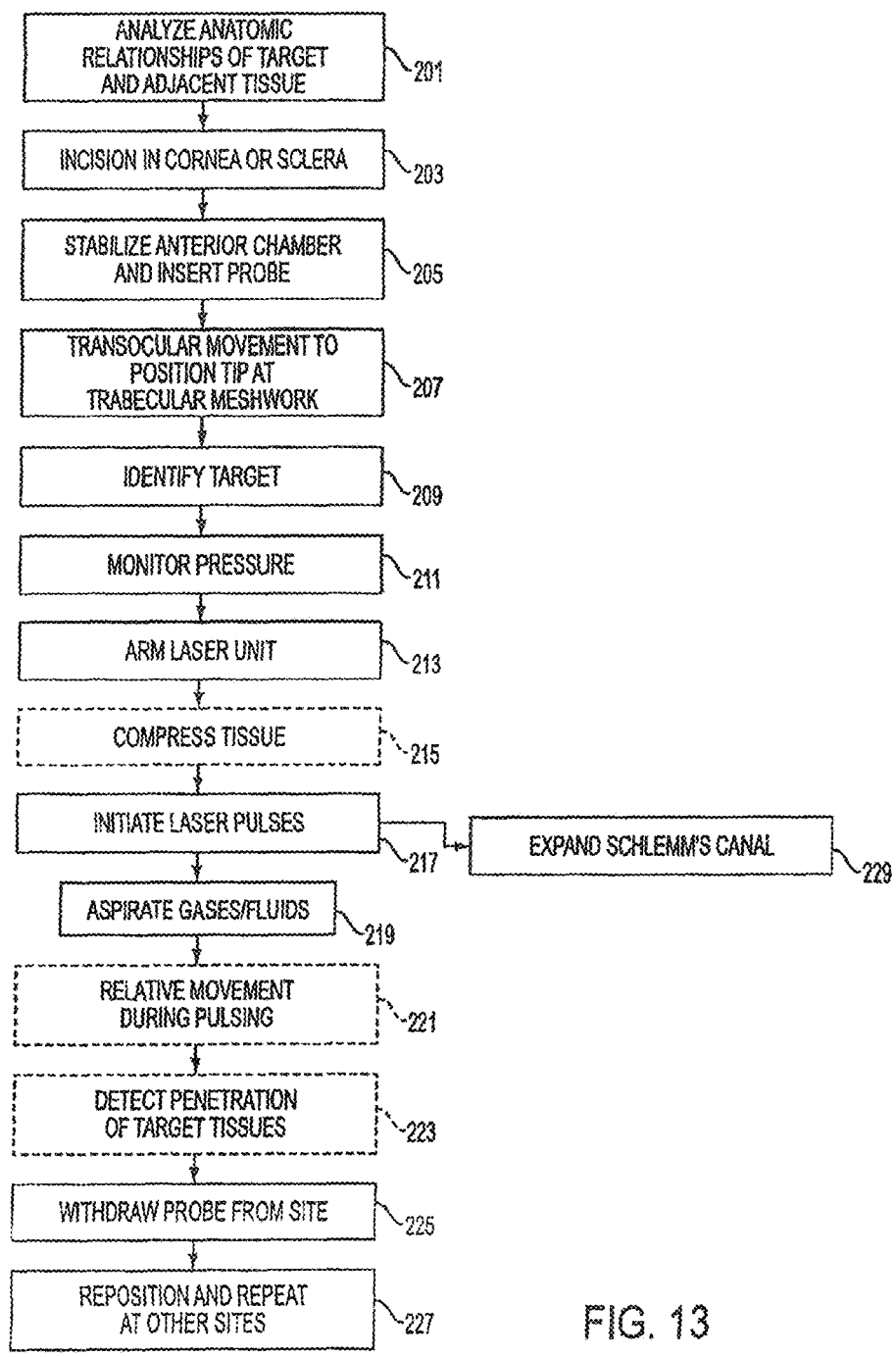
FIG. 13 is a block diagram of an embodiment of a method of treating glaucoma with a laser delivery system.

Referring to FIGS. 3 and 13, an overview of a method of operating laser delivery system 21 for treatment of glaucoma or other eye conditions follows. FIG. 3 is a side sectional view of the interior anatomy of a human eye showing fiber-optic probe 23 in relation to an embodiment of a method of treating glaucoma. After applying local and/or retrobular anesthesia to eliminate pain, a small self-sealing incision 14 can be created in the cornea 15 with a surgical blade or other device. The anterior chamber can be further stabilized with a viscoelastic agent. Fiber-optic probe 23 can then be positioned and advanced in the incision 14 into the anterior chamber 7 until a distal end of fiber-optic probe 23 contacts or is substantially adjacent to the desired target tissues for removal.

Laser energy produced by laser unit 31 is delivered from the distal end of fiber-optic probe 23 in contact or adjacent to the tissues sufficient to cause photoablation of tissues. Tissue to be ablated can include the trabecular meshwork 9, the juxtacanalicular trabecular meshwork 13 and an inner wall of Schlemm's canal 11. Fiber-optic probe 23 can be advanced towards Schlemm's canal 11 and creates an aperture in the proximal inner wall of Schlemm's canal 11, but does not perforate the distal outer wall. In some embodiments, additional apertures can be created in the trabecular meshwork and target tissues. Thus, the resultant aperture or apertures are effective to restore relatively normal rates of drainage of aqueous humor.

Referring to FIG. 4, fiber-optic probe 23 is illustrated having similar structure as structure disclosed in U.S. Pat. No. 4,846,172, to the present inventor, which is herein fully incorporated by reference. In some embodiments, probe 23 includes an axially disposed light transmitting core 33 having an optical fiber or a plurality of optical fibers 35 in which core 33 is stiffened by an encapsulating sheath 37. The diameter of a single optical fiber 35 should be sufficiently large to transmit sufficient light energy to effectively result in photoablation of target tissues. In some embodiments, the optical fiber diameter is in a range from about 4-6 mm. A single optical fiber or a plurality of optical fibers 35 can be used in a bundle of a diameter ranging from about 100 μm to about 1000 μm, for example. Core 33 and sheath 37 can be encased within an outer metal sleeve, or shield 39. In some embodiments the sleeve is fashioned from stainless steel. In some embodiments, the outer diameter of sleeve 39 is less than about 1000 μm. In some embodiments, the diameter can be as small as 100 μm, as where smaller optical fibers are implemented with laser delivery system 21. In some embodiments, the sleeve can be flexible so that it can be bent or angled.

The tip or distal end 41 of probe 23 can be inclined with respect to a central longitudinal axis 43 extending between distal end 41, and a proximal end 45, of the probe. The angle of the inclination can range from about 0 degrees to about 180 degrees. In some embodiments, the angle of inclination is conveniently in a range from about 30 degrees to about 60 degrees. The inclined geometry can be configured to orient the distal end 41 of probe 23 relative to the surface of the target tissues, so that photoablative decomposition of target tissues can proceed uniformly, and so that distal end 41 of probe 23 is oriented to enable photoablation of the target tissues.

In some embodiments, the tip 47 of the optical fiber, or fibers 35, are configured to emit a beam of light with controlled divergence, such that a laser spot size encompasses a larger target area than the fiber cross sectional diameter. This enables the formation of perforations, or apertures, in target tissues that have a larger diameter than the probe sleeve 39. This configuration also effective to reduce thermal damage to tissue.

Figure 5A:
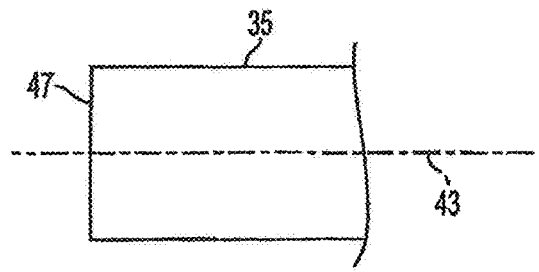
FIGS. 5A-5P are schematic diagrams of some embodiments of a tip of a fiber-optic probe.
Figure 5B:
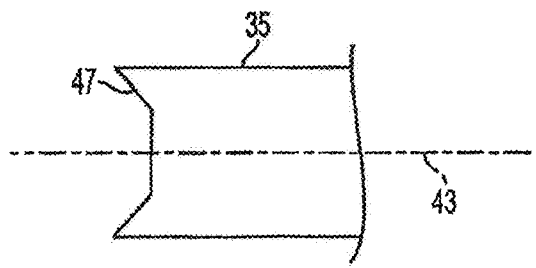
Figure 5C:
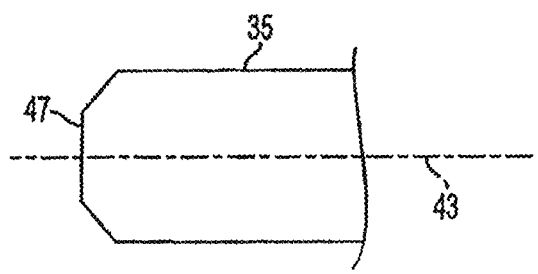

In some embodiments, tip 47 of the optical fiber or fibers 35 is shaped such that each tip has a unique energy distribution, and therefore is best suited to a particular need. In same embodiments, for example, as shown in FIGS. 5A-5P, fiber tip 47 can be shaped in a plane normal to the longitudinal axis 43 (see FIG. 5A), in a concave shape (see FIG. 5B), or in a convex shape (see FIG. 5C), thus providing a range of possible spot sizes where the beam contacts the target tissue.

Figure 5D:
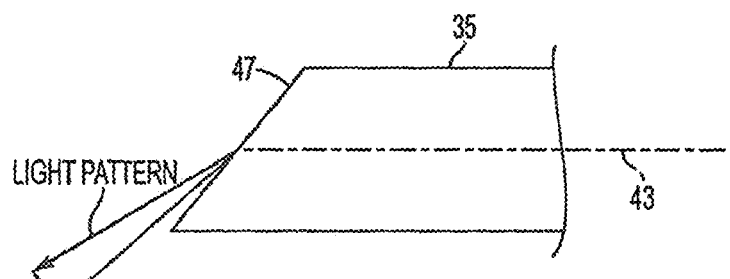
Figure 5E:
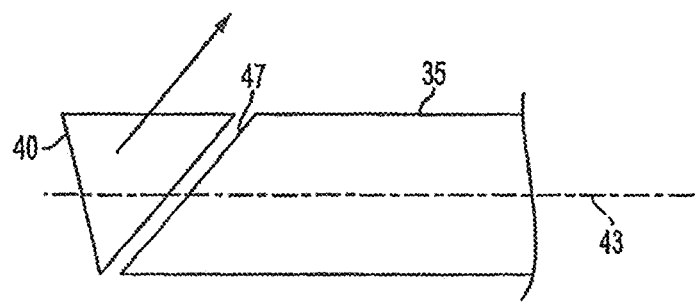
Figure 20A:
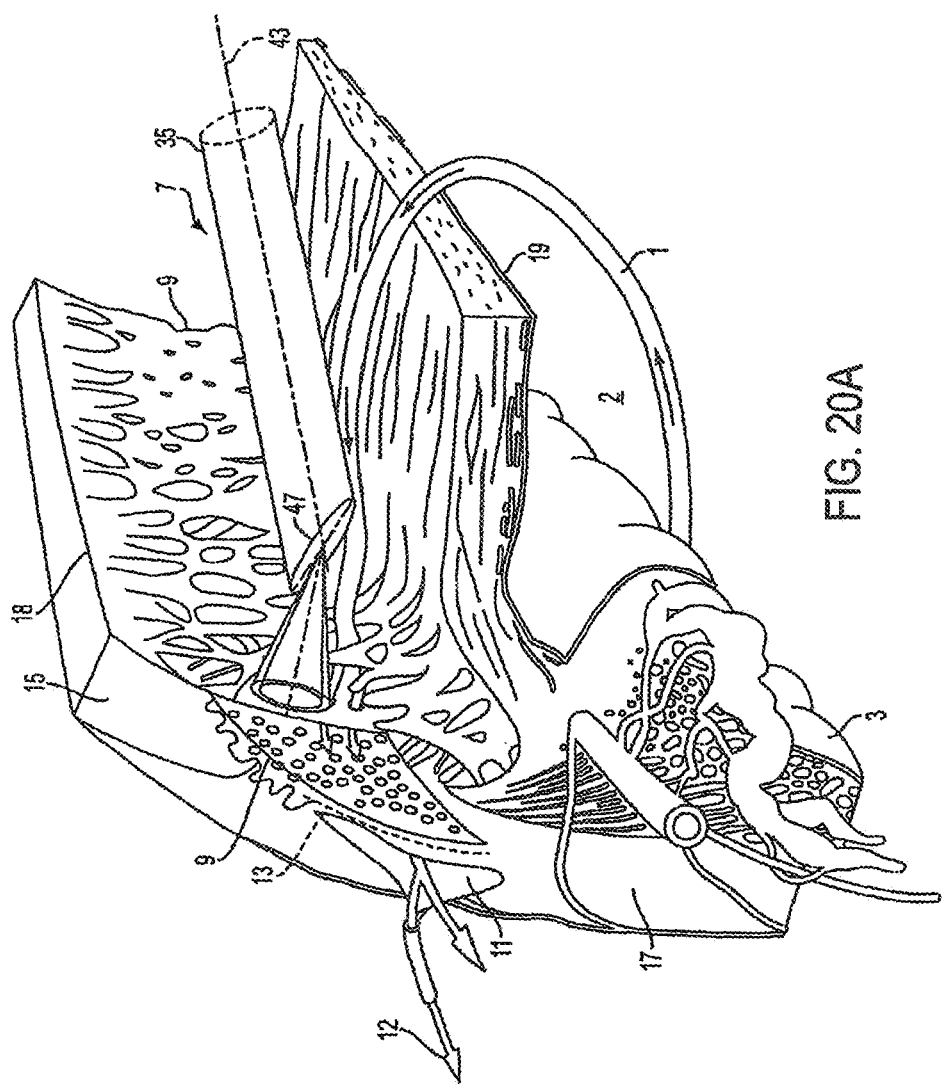
FIGS. 20A-20B are schematic diagrams of an embodiment of a beveled face fiber-optic tip performing a photoablation treatment of a tissue.
Figure 20B:
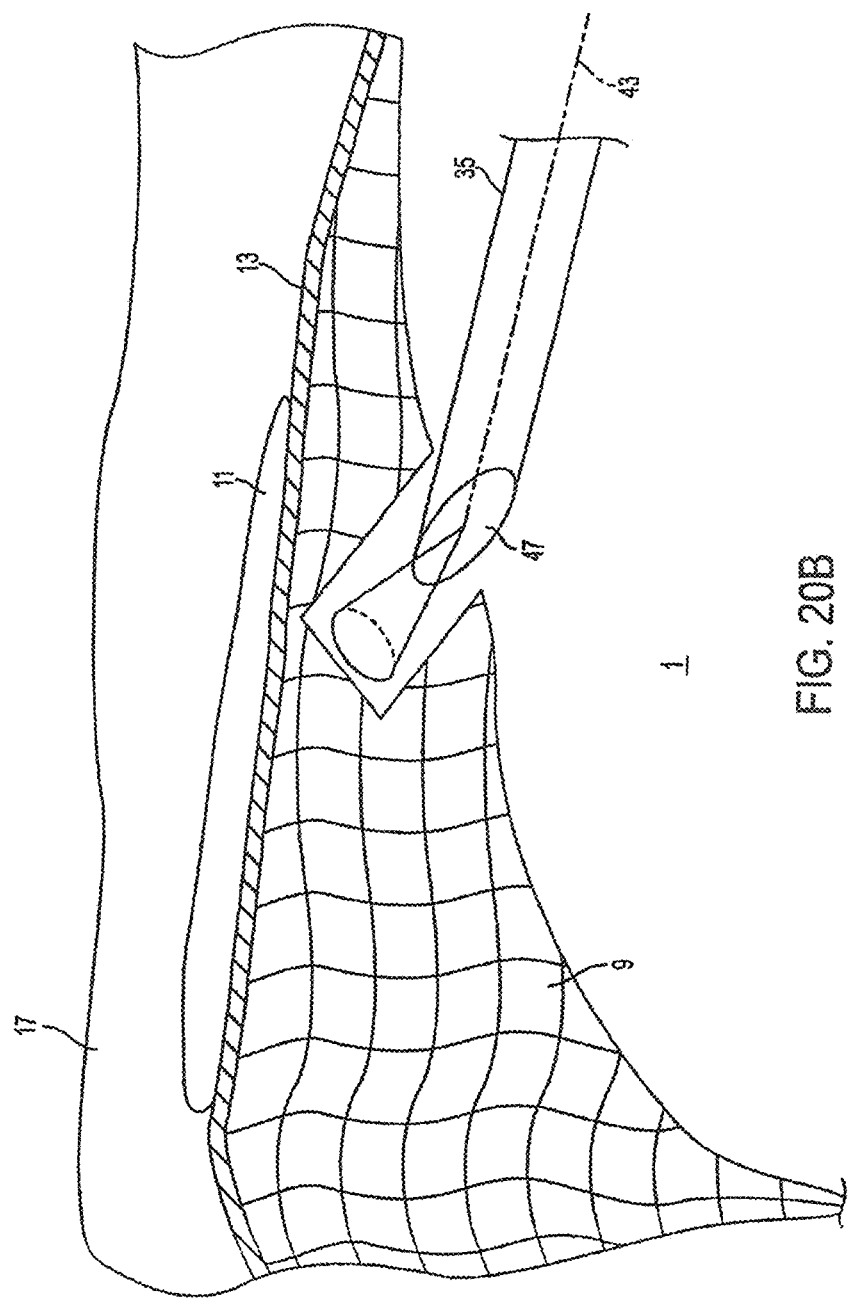

In addition to controlling laser spot size, it can also be desirable to control the direction of the laser energy being delivered from distal tip 47. As shown in FIG. 5D, distal fiber tip 47 can have a beveled face to enable formation of a downward directed cone shaped pattern of light. As shown in FIG. 5E, a beveled faced distal fiber tip 47 can further include a microprism 40 that provides directional control of the light pattern. As shown in FIGS. 20A-B, a cone-shaped laser energy distribution is delivered from the beveled faced fiber tip 47 such that fiber tip 47 can be oriented for precise photoablation of the target tissues. In some embodiments, the inclined shape of distal end of probe 23 can be aligned with beveled face fiber tip 47. Fiber tip 47 can extend beyond distal end 41 to enable more precise control over the procedure.

Figure 5F:
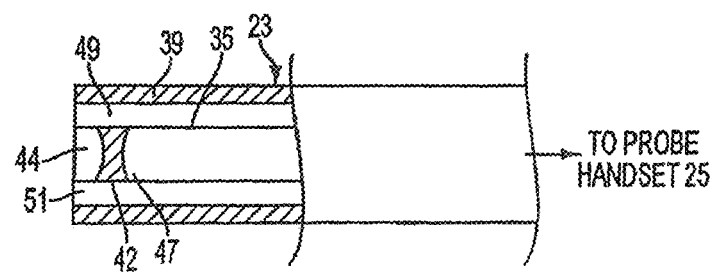

Other mechanisms can be used to control the laser spot size. For example, and as shown in FIG. 5F, a transparent spacer or window 44 can be abutted by a micro lens 42 (or a microprism), attached to distal fiber tip 47, to achieve a desired spot size of the laser energy on the target tissues. Micro lens 42 is designed such that the target area or spot size, energy distribution and direction of the laser energy can be controlled. Spacer 44 prevents fiber tip 47 from contacting target tissues during the photoablation process. Such arrangement reduces any likelihood that waste products from the process are deposited on the fiber tip 47. Fiber tip 47 can also be maintained free of waste material collecting on it by providing a gas or fluid flow, including a viscoelastic fluid, across the tip. It should be recognized that micro lens 42 and the spacer are generally sized so as to match the diameter of the attached optical fiber.

In some embodiments, as illustrated in FIG. 4, an irrigation fluid, such as a saline solution, can be provided to cool the target tissues, and to reduce or control possible damaging thermal effects on the target tissues. The irrigation fluid can be aspirated from the eye to prevent overpressure or to remove vent gases formed during photoablation. In some embodiments, as described below, the evolution of vent gases during the process of photoablation, has been found to be a useful indicator for confirming a channel has been formed in the trabecular meshwork. Fiber-optic probe 23 can include side-by-side semicircular passageways within and along the interior of sleeve 39 forming an irrigation flow path 49 and a separate aspiration flow path 51.

Figure 19:
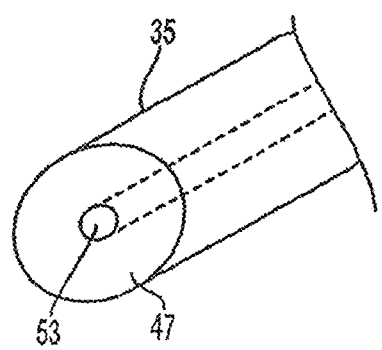
FIG. 19 is a schematic diagram of an embodiment of an irrigation system for use with a laser delivery system.

Distal end 41 of probe 23 includes terminal openings for flow paths 49, 51 at distal end 41. These openings can also be positioned along the probe near the terminal end. The terminal openings can be coaxial or in an angled relationship to the light transmitting core 33. Proximal end 45 of probe 23 links flow paths 49, 51 into corresponding flow paths in handset 2. The coupling can be accomplished by known approaches for laser probes. Although the irrigation and aspiration flow paths 49, 51 have been described been in a side-by-side relationship within the sleeve 39 they can also be provided as concentric tubes about a central optical fiber or the infusion/aspiration path flow can be central and the optical fiber adjacent its periphery. As shown in FIG. 19, in some embodiments, a fiber-optic core 33 can have a hollow cylindrical pathway 53, extending along the center axis for providing irrigation or aspiration pathway as needed. In some embodiment, flow path construction based on fiber-optic advances can be employed with optical fibers up to about 100 μm. Also, other specialized fibers can enable the associated irrigation and aspiration passageways to be arranged in other ways including within the fiber core(s).

Continuing to refer to FIG. 4, flow paths 49, 51 in probe 23 can be connected to an irrigation system 55 and an aspiration system 57 of laser delivery system 21. Each system 55, 57 will be described in detailed herein. Irrigation system 55 supplies a desired irrigation fluid into probe handset 25 via a flexible tubular line under a gravity-feed configuration or a pumped configuration. In the case of a pump configuration, the irrigation fluid can be pumped from a sterile reservoir or container 24 into handset 25. The fluid can then flow under pump pressure in irrigation pathway 49 to probe 23 distal end 41 and to target tissues.

In some embodiments, a viscoelastic fluid, or other fluid, from the irrigation system 55 can be pumped into handset 25 and into probe 23 for cooling the target site. In some embodiments, a viscoelastic fluid can be used to compress or flatten the trabecular meshwork in the eye, to control its dimensions. In some embodiments, viscoelastic materials having a molecular size that is larger than the pore size of the target tissues are used in conjunction with the described methods, making it possible to tampanade, or push on, the tissue, rather than having the fluid simply diffuse into the tissue. Through selection of particular viscoelastic fluids the trabecular meshwork 9 (see FIG. 2) can be compressed to a reduced thickness, and in turn stabilized for eventual removal of selected portions of tissue by laser photoablation.

In some embodiments, a viscoelastic fluid can include combinations of therapeutic agents to prevent inflammation at the target site, thus keeping patent surgically formed apertures. For example, and without being limiting, a viscoelastic fluid or other fluid (where a fluid can comprises a liquid or a gas) can be combined physically and/or chemically with, anti-inflammatory agents, steroidal and non-steroidal, anti-angiogenic agents, anti-fibroblast agents, and various other combinations of agents. Examples of these types of agents include, without limitation, DFU, a non-steroidal anti-inflammatory, anecortave acetate, an angio-static steroid analog of cortisol acetate, or anti-TGF, a monoclonal antibody known to inhibit all three forms of TGF-β. An example of an available viscoelastic material having a non-steroidal anti-inflammatory agent is disclosed in U.S. Pat. No. 5,811,453 to Yanni et al., the entire contents of which are herein incorporated by reference.

Figure 6:
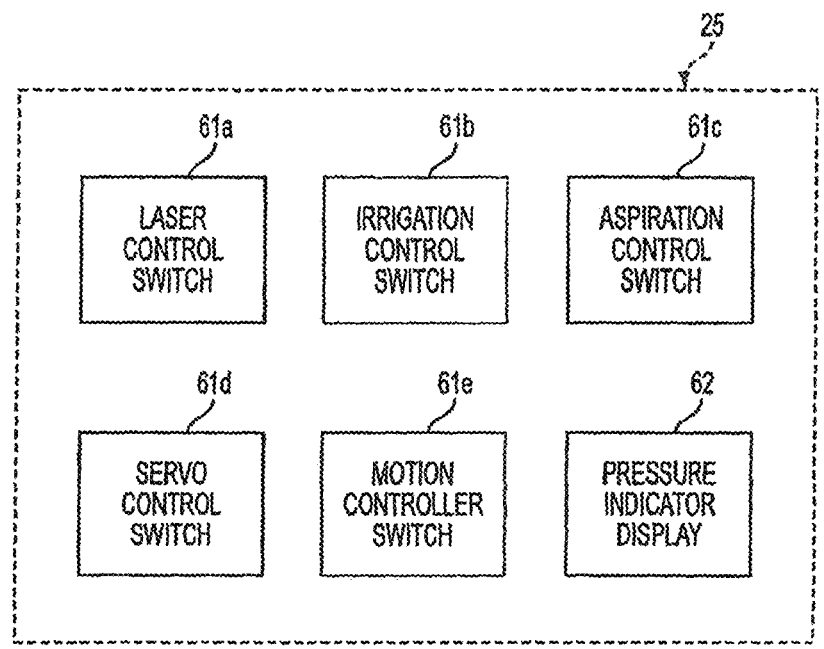
FIG. 6 is a schematic diagram of an embodiment of control switches as can be provided on a handset controller for a fiber-optic probe.

In some embodiments, control switches 61 on the handset 25, a foot pedal, or other control device can be used by the surgeon to initiate flow of the fluid by valve and/or pump control. Irrigation fluid flow can be commenced along with the laser energy delivery to the target tissues. In some embodiments, coordination of the flow of fluid with the startup of the laser unit 31 can be automatically regulated by other devices. For example, as shown in FIG. 6, handset 25 can include a plurality of control switches 61a-61 for operating laser delivery system 21.

Control switches 61a-61e perform the same or all of the following functions for operating laser delivery system 21, such as switch 61a for arming and firing laser unit 31; switch 61b for controlling irrigation system 55; switch 61c for controlling aspiration system 57; switch 61d for controlling servo device 27; and switch 61e for controlling motion controller 29. The control switches optionally can be mounted on a separate unit, such as a remote control unit.

Aspiration system 57 enables the extraction of fluid from the eye and also enables immediate extraction of the gases generated from the photoablative decomposition process to escape through aspiration flow path 51 through flexible lines in handset 25. Aspiration system 57 can function passively or can include a sufficiently sized vacuum pump for enabling waste fluid to be auctioned into a waste container or canister 58. Aspiration system 57 allows gases to be removed without otherwise heating the local tissues. Thus, aspiration system 57 advantageously reduces thermal tissue damage.

Laser delivery system 21 can further include a laser unit 31 for providing a beam of periodic light pulses of sufficient fluence to initiate and sustain photoablation of the target tissues in contact with distal end 47 of probe 23. In some embodiments, laser unit 31 comprises a xenon chloride excimer laser operating at a 308 nm wavelength having a fluence ranging from about 1 to about 60 mJ/mm$^2$ per pulse and a repetition rate ranging from about 5 to about 75 Hertz. The corresponding repetition rate can be varied to compensate for the thermal time constant of the tissues in relation to the fluence of the laser energy radiating the target tissues. Conveniently, the 308 nm wavelength is absorbed by eye tissues more so than by any intervening aqueous humor or any viscoelastic fluid between the tissues, ensuring optimal delivery of energy to the tissue to be photoablated.

The previously described laser parameters significantly reduce the thermal component of the laser energy and accordingly, resultant collateral tissue damage is minimized. In some embodiments, the laser unit 31 can be a solid state 2.94 μm Er:YAG laser. This wavelength can be delivered to the target tissue through probe 23 via light transmitting core 33. In addition, laser unit 31 can include a safety circuit to preclude inadvertent triggering. The various laser parameters can be adjusted accordingly to calibrate laser unit 31 for use on a variety of target tissues. A 355 nm solid state laser can also be used as laser unit 31. One of ordinary skill in art can consider calibration factors such as the homogeneity of the output of the light beam, minimizing the pulse-to-pulse energy variation, the suprathreshold fluence value, and reducing the thermal component of laser-tissue interaction, in designing laser units for use in tissue photoablation procedures.

In some embodiments, a laser operating at wavelengths in the ultraviolet range from about 100 μm to about 400 μm can be utilized to cause photoablation of a target tissue. In some embodiments, a laser operating in the infrared wavelengths, for example, in a range from about 2.5 to about 6.5 μm can comprise a laser unit 31. In seeking to minimize the thermal damage to target tissues, if the temperature in the target site reaches a predetermined level established as undesired, then the periodic time between pulses can be lengthened in the range from about 5 to about 20 Hz, to permit sufficient cooling between successive application of light energy.

Generally, for use with embodiments described herein, the lasers can have a short penetration depth, which allows for sufficient precision per laser pulse and controlled energy distribution. With ultraviolet lasers, the penetration depth can typically be in a range from about 0.5 to about 1.5 μm, while for infrared lasers, the penetration depth is typically in a range from about 1-2 μm.

Figure 7:
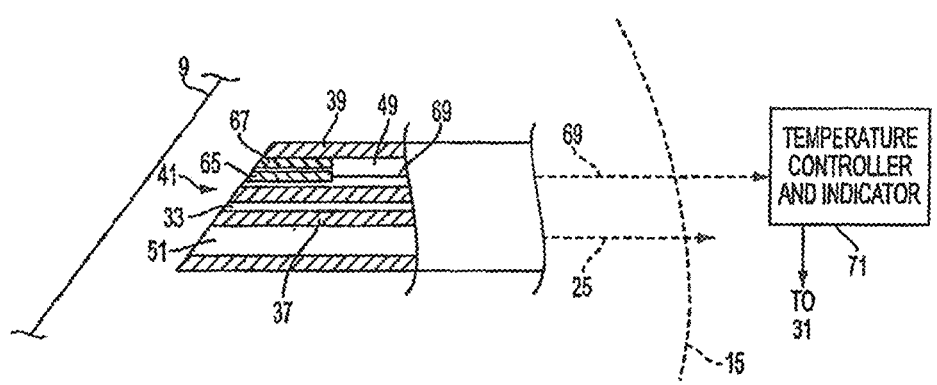
FIG. 7 a schematic diagram of an embodiment of temperature sensing circuitry of a laser delivery system.

In some embodiment, one of which is illustrated in FIG. 7, laser delivery system 21 can include temperature measurement circuitry for sensing temperature at, or in the vicinity of, the target site, and for minimizing collateral thermal damage at and around the target tissues. In this example, distal end 41 of probe 23 can include a thermocouple 65 that is thermally isolated from sleeve 39 by an insulating pad 67. Thermocouple 65 and insulating pad 67 can be sized for use with probe 23. Conductors 69 from the thermocouple 65 can extend through probe 23 to transmit a feedback signal to an external controller 71. The external controller 71 can indicate or otherwise display the internal temperature sensed by thermocouple 65. In some embodiments, controller 71 alerts the surgeon when the temperature exceeds a predetermined level.

If some embodiments, external controller 71 can be operatively coupled to laser unit 31 to permit automatic self adjustment of the repetition rate of the laser based on the sensed temperature, or to provide for automatic shutoff of the laser should the temperature in the vicinity of the target site exceed a predetermined value. This enables external controller 71 to operate to minimize the thermal effect on the target tissues. The probe sleeve can be cooled externally near the handpiece. Cooling flow can be conducted along the sleeve to affect the probe tip and adjacent tissues.

Figure 21A:
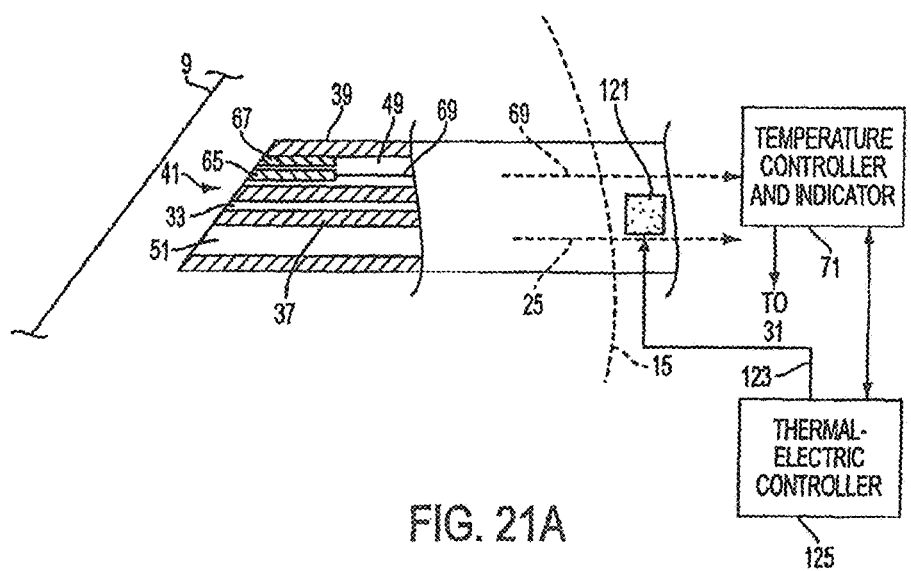
FIGS. 21A-21B are schematic diagrams of some embodiments of heat extraction systems.

Fiber-optic probe 23 can also include a heat extraction system for reducing the thermal component of the laser-tissue interaction during the photoablation period. By removing heat, the heat extraction system can be used to complement the minimal thermal tissue removal of laser unit 31 in order to reduce collateral damage to target tissues from the laser energy. The heat exchanging system can cool sleeve 39 of probe 23 by a heat sink. In an exemplary configuration, the heat sink can be a cooling working liquid that flows in the interior of probe sleeve or cools the probe sleeve by conduction from the handpiece. In some embodiments, for example, as shown in FIG. 21A, an appropriately designed thermoelectric device 121 can be mounted in the interior of the probe 23 or the handpiece 25, for example, a Peltier device. Thermal electric device 121 can be sealed from the fluid in aspiration pathway 51. Device 121 can be coupled to tubular sleeve 39 such that heat can be removed from the surrounding fluid in the eye contacting probe 23. In some embodiments, device 121 can be fluid- or water-cooled such that fluids flowing in aspiration pathway 51 transfer heat from device 121 to waste container 58.

Figure 21B:
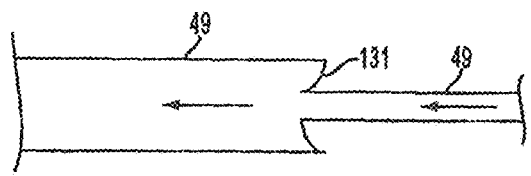

In some embodiments, thermal electric device 121 can be mounted on the exterior of tubular sleeve 39 near proximal end 45 in handset 25. In such a case, device 121 can be air cooled for transferring extracted heat to the air. In both cases, signal wire 123 provides electric power to operate device 121 and extends to a thermal electric controller 125. Controller 125 is configured to control the operation of device 121 by turning electric power on and off. Controller 125 can be coupled to external controller 71 in order to operate thermal electric device 121 when the sensed temperature in the eye reaches a predetermined level. A thermal insulating sleeve can be provided on the exterior of tubular sleeve 39 to prevent cooling of the comes and/or the anterior chamber by probe 23. The thermal insulating sleeve can extend near the proximal end of probe 23. In some embodiments, cooling can be achieved by Venturi cooling or convection cooling. Referring to FIG. 21B, with Venturi cooling, a Venturi orifice 131 can be mounted in irrigation pathway 49. One skilled in the art would recognize various other ways to cool the probe can be performed.

Figure 8A:
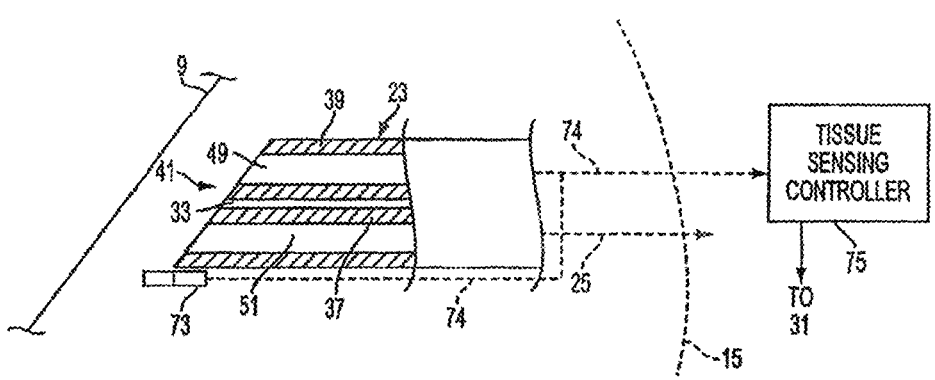
FIGS. 8A and 8B are schematic diagrams of some embodiments of tissue sensing circuitry in a laser delivery system.

In some embodiments, referring to FIG. 8A, laser delivery system 21 can include tissue sensing circuitry for determining when fiber-optic probe 23 is adjacent to or in contact with tissues in the target site. In an exemplary arrangement, distal end 41 of probe 23 includes a microswitch 73 for sensing physical contact with tissues, for example, the trabecular meshwork 9. Microswitch 73 can be constructed from a biocompatible material suitable for internal use. Microswitch 73 can be formed in a number of configurations as long as a contact signal is transmitted via signal wires 74 to controller device 75. Signal wires 74 can be installed in a small liquid-tight conduit inside of probe 23 that extend to the proximal end. The contact signal can be a completion of an electrical circuit between switch 73 and controller device 75. Controller device 75 processes the contact signal, which can be used both to alert the surgeon that probe-tissue contact has been achieved, and in a feedback loop to control laser functions. The alert can be in the form of a lighted display, sound, or other indicator. In addition, the tissue-contact signal can be processed to prevent triggering of laser unit 31 until tissue contact is achieved. As a result, undesired firing of laser unit 31 is avoided, thus reducing the chance of overheating the aqueous humor or other fluid in the anterior chamber. It will be appreciated that the tissue-contact signal ceases when microswitch 73 is deactivated by not being in contact with the tissue. In some embodiment, a sensor can detect contact of the laser probe with the tissue surface to be ablated.

Figure 8B:
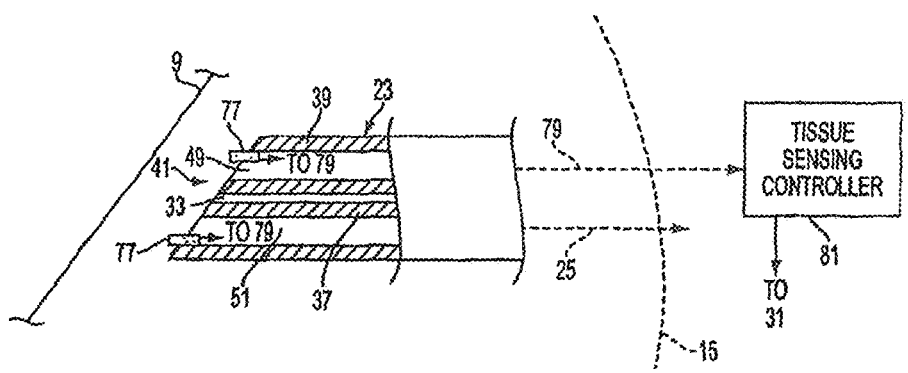

In some embodiments, contact with the eye tissue, such as the trabecular meshwork, alternatively can be detected by a pair of microelectrodes 77 mounted on an insulator substrate at distal end 41 of probe 23, as shown in FIG. 8B. Microelectrodes 77 can be coupled to signal lines 79 that extend along sleeve 39 to an external gap detector circuit 81. The circuit 81 can respond to a threshold change in conductivity or capacitance when the target tissues, for example, the trabecular meshwork, are contacted or within an adequately small distance from the tip. Distance can be defined as a function of the dielectric using the probe as one plate and the tissue as a second plate of a capacitor. In order to detect a change in conductivity or capacitance, it is recognized that the aqueous humor and the trabecular meshwork possess different dielectric values. When probe 23 enters the anterior chamber 7, the electrodes 77 are located in the aqueous humor, as shown in FIGS. 3 and 8B. When microelectrodes 77 enter or contact the trabecular meshwork, for example, the dielectric value between the electrode changes. As a result, there is corresponding change in capacitance indicating that probe 23 has contacted tissue.

Laser delivery system 21 can include circuits for preventing the firing of laser unit 31 when the fiber tip 47 is too far separated from the target tissue in order to prevent undesirable thermal heating of aqueous humor and/or the viscoelastic fluid. This can be achieved by the probe-tissue contact signal generated by microswitch 73 (See FIG. 8A) located at distal end 41 of probe 23. The probe-tissue contact signal is triggered by conductivity changes occurring to tissue compression and relative tissue/aqueous composition. Alternatively, probe-tissue contact signal or a proximity signal, as previously described, can be generated by microelectrodes 77 (See FIG. 8B) located at distal end 41 of probe 23 to prevent firing of laser unit 31. Also, the handset 25 can use the signal to activate the laser unit 31 or allow it to be fired if further closure of the gap is needed.

Figure 9:
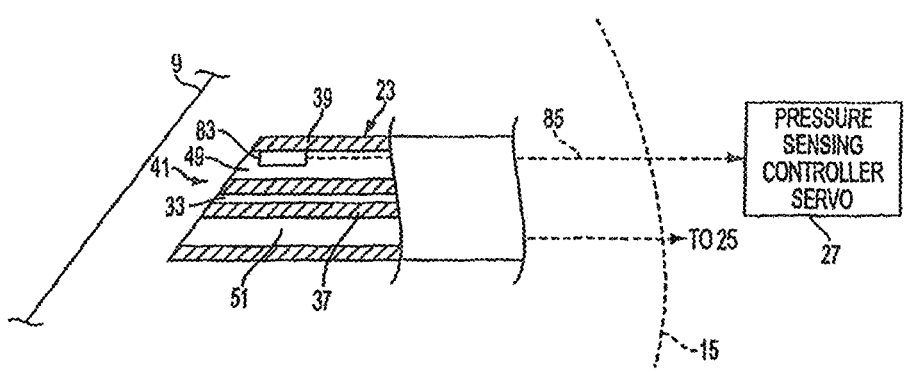
FIG. 9 is a schematic diagram of an embodiment of pressure sensing circuitry in a laser delivery system.

Turning to FIG. 9, laser delivery system 21 can include pressure sensing circuitry for detecting and controlling pressure at the surgical site, and within the anterior chamber, during an ophthalmic procedure. Distal end 41 of sleeve 39 can include a pressure sensing transducer 83 for transmitting a feedback pressure signal via signal wires 85 to servo device 27 in order to control the pressure so that target tissue manipulation can be controlled. Signal wires 85 extend from the distal end to the proximal end of probe 23 for operatively coupling to handset 25 and servo device 27. Similar to the tissue sensing circuitry embodiment, signal wires 85 can also be in a liquid-tight conduit located inside of the probe. It will be recognized that the pressure sensing transducer can also be located near the probe tip or in the irrigation pathway, and in addition, can be located proximal to the tip along the probe within the anterior chamber.

Figure 10:
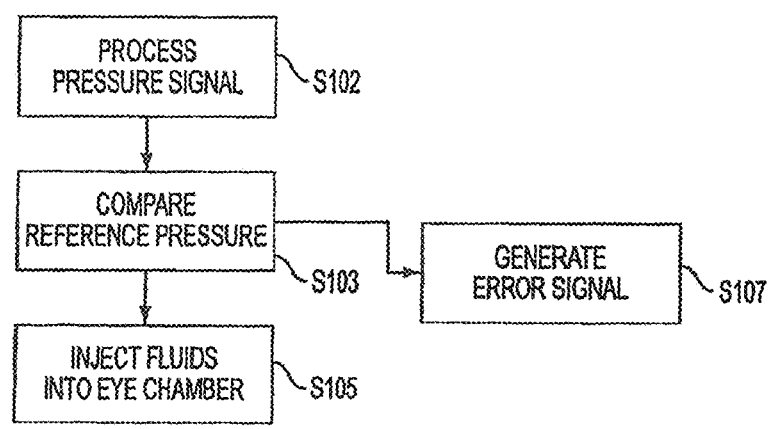
FIG. 10 is a flow chart of an embodiment of operating a servo device of a laser delivery system.

Referring to FIGS. 4 and 10, servo device 27 can include a microprocessor circuit having associated operating software for reading the pressure signals and translating the signals into machine readable code. This can be accomplished with appropriate analog to digital converter devices, as are known in the art. Servo device 27 can continuously monitor and regulate the pressure during an ophthalmic procedure, in particular a method of treating glaucoma. Referring to FIG. 10, in order to regulate pressure, in step S101, servo device processes pressure signals from pressure sensors 83. In step S103, the pressure signals can be compared with a pro-determined reference pressure. In step, S105 servo device 27 injects fluids, such as a viscoelastic fluid, into anterior chamber 7 of the eye in order to maintain the reference pressure or to adjust to a target pressure level. In addition, in step, S107, servo device 27 can generate an error signal when the sensed pressure level becomes other than the desired reference level. Optionally, a pressure indicator display 62 can be located on handset 25. Pressure sensor 83 can be located at a distal end of probe 23. In addition, pressure sensor 83 can be located along the shaft of probe 23. Optionally, more than one pressure sensor can be mounted on probe 23 at various locations.

Figure 11A:
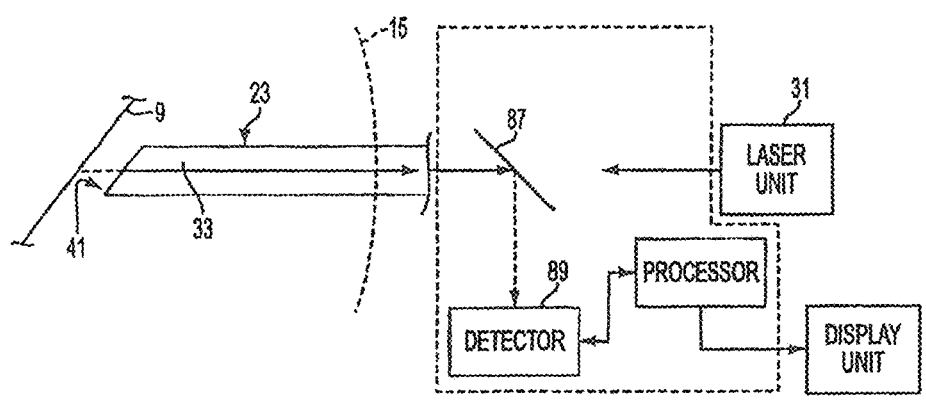
FIGS. 11A-B are schematic diagrams of some embodiments of tissue guidance circuitry in a laser delivery system.

Laser delivery system 21 can also include tissue recognition guidance circuitry for detecting penetration into Schlemm's canal by advancement of fiber-optic probe 23 or by laser energy. The tissue recognition guidance circuitry provides information regarding where the probe is located relative to target tissues. In one arrangement, as illustrated in FIG. 11A, a form of optical spectroscopy is employed in which laser light pulses reflected from the target tissues create a back-scattered signal. Optical spectroscopy measures the interaction of light within tissues and provides information for diagnosis at the structural and pathophysiologic level with intact tissues, as is known in the art.

The back-scattered signal can be deflected by a dichroic mirror 87 in-line with an optical fiber 33, which can be the same fiber used to transmit the laser light or a separate detection fiber to an appropriate detector 89. This enables precise identification of the spatial movement of the fluid, for example, from the anterior chamber to the interior of Schlemm's canal. Alternatively, as part of the optical spectroscopy, a separate optical fiber for returning the back-scattered signal to the detector can be employed. In either case, as is known in optical spectroscopy, the back-scattered signal provides information concerning the relative positions of the probe and the target tissues. Photoacoustic spectroscopy can be used in place of optical spectroscopy. In photoacoustic spectroscopy, incident light is modulated to generate acoustic frequencies. In either case, light signals can be reflected off the target tissue generating a signal reflecting the relative position of the probe to the target tissues. It should be noted that it can be possible to determine the location of the probe relative to target tissues by direct visualization though the primary and or accessory optical fibers.

Figure 11B:
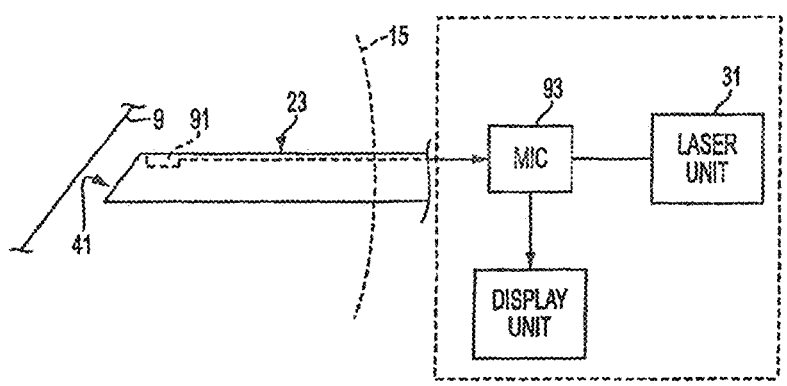

In some embodiments, one of which is illustrated in FIG. 11B, a form of photoacoustic spectroscopy, which allows tissue imaging and depth profiling as is known in the art, implements an acoustic pulser 91 for transmitting signals along the probe 23 to a sensitive capacitive microphone 93, to sense the generated pressure fluctuations. The generated echo would be in a frequency range less than about 50 KHz. The principles of photoacoustic spectroscopy are well known in ophthalmology.

Figure 12:
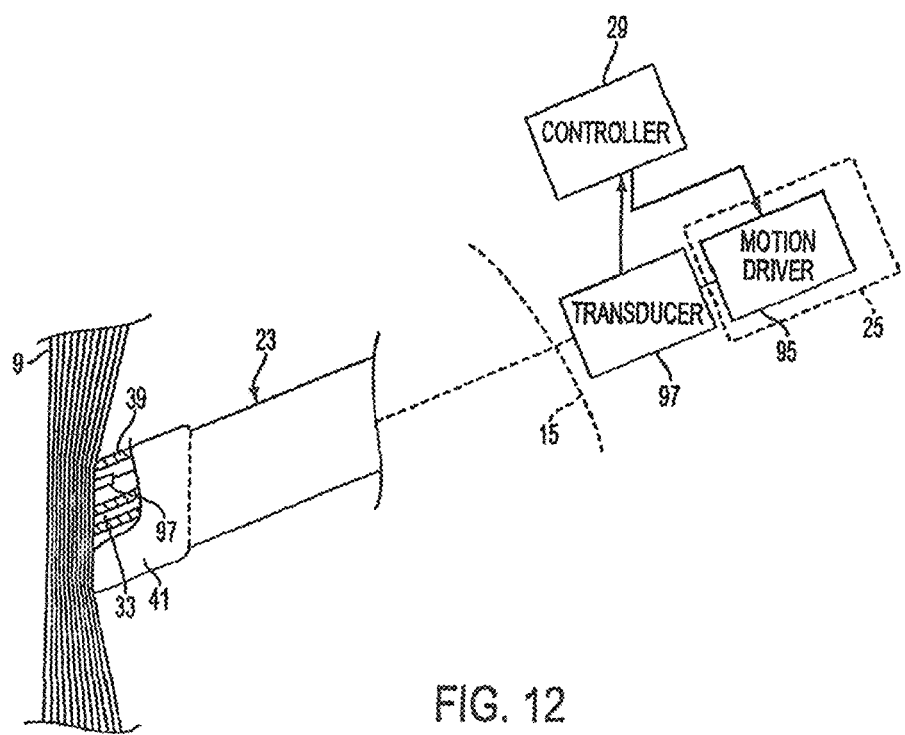
FIG. 12 is a schematic diagram of an embodiment of a motion controller for a fiber-optic probe.

Referring to FIG. 12, laser delivery system 21 can further include motion controller 29 for enabling a controlled rectilinear movement of probe 23 into and through a target tissue site, such as the trabecular meshwork. This is achieved by blunting a portion of distal end 41 of probe 23 to enable sufficient contact against target tissues, such as the trabecular meshwork, with a controlled force produced by a mechanical or hydraulic apparatus. Motion controller 29 can include a limited motion driver 95, such as one using a sensitive miniature voice coil, employed in handset 25 to move the blunt and of probe 23 against the tissues, such as the trabecular meshwork, at a controlled rate and through a precise distance.

A force transducer system 97 senses the axial force applied to the tissues when a reactive resistance force is increased. The motion controller 29 slows probe movement when the tissues are compressed to a desired thickness. This type of automatic system provides precise controlled movement and operates more steadily than a manually operated probe. One skilled in the art would recognize various hydraulic or mechanical and controllable systems can be used for the purpose of moving probe 23 in a controlled movement. Motion controller 29 thus proves for controlled movement with micron precision. As illustrated in FIG. 12, precise controlled movement as provided with an automatic system can be useful for compressing the trabecular meshwork 9.

Distal end of fiber-optic probe 23 can include a device for viewing probe contact with target tissues. Such a device can have an optical fiber particularly used for viewing the target site, similar to that used in an endoscope that facilitates the viewing. A non-coaxial endoscope can also be used. Positioning can be detected by direct view, or by increasing the intensity of backscattered light or by interferometry.

FIG. 13 illustrates an example of a method of facilitating the drainage of aqueous humor by creating a flow pathway via, or circumventing, the trabecular meshwork and juxtacanalicular trabecular meshwork, into Schlemm's canal of an eye in order to reduce intraocular pressure. Generally, a distribution of spaced apart radial passages in the periphery of the eye is established to ensure relief of intraocular pressure. In step 201 of FIG. 13, the anatomic relationships of the target and adjacent tissues are analyzed. In particular, anatomic landmarks are identified and relationships between those landmarks are noted. Available equipment employing ultrasonic spectroscopy and optical coherent tomography can be utilized for anatomic tissue localization both prior to and during the method. Once the anatomic factors are determined, the surgeon can visualize and study the position of the visible trabecular meshwork through a goniolens 97 and a typical operating microscope used in ophthalmic surgery. The surgeon is ready to continue with the procedure once landmarks such as Schwalbe's line, the scleral spur and possibly Schlemm's canal, are identified.

Referring to FIGS. 3 and 13, in step 203, a small self-sealing incision, or paracentesis opening 14, is made in the cornea 15, or sclera 17, to allow access to the target site. The small size of the initial opening in the cornea, or the sclera, introduces a minimal entry trauma, and in most instances the small size self closes without suturing. In step 205, the anterior chamber is stabilized with viscoelastic and fiber-optic probe 23 is advanced into the opening 14 and into anterior chamber 7. At step 207, probe 23 is advanced through the anterior chamber according to transocular movement to position distal end 41 of probe 23 in contact with or adjacent to trabecular meshwork 9. A determination of whether probe 23 should be in contact with or adjacent to trabecular meshwork 9 can depend on the physical characteristics of the particular site and is made by the surgeon and is within ordinary skill in the art. For the purpose of the present invention, the probe 23 should be within an operable limit of the trabecular meshwork, that is, it should be in contact with or adjacent to the trabecular meshwork in order to enable photoablation at the target tissues, as determined by one of skill in the art.

In step 209, a desired target area is identified so as to position distal end 41 of probe 23 in a direction relative to Schlemm's canal 11 in order to penetrate its inner wall adjacent to the anterior chamber. Positioning distal end 41 of probe 23 will depend on the energy distribution of the selected probe tip 47. As previously described, numerous probe tip designs can be used, depending on the surgeon's determination. Several techniques can be used to identify the desired target tissues. In one technique, if Schwalbe's line 18 (FIG. 8) is visible, then a measurable reference exists that can be used to relate to the length of sleeve 24 at its distal end. More specifically, probe 23 can be positioned at the identified anatomic landmark, such as Schwalbe's line 28. Alternatively, a radial indicator, such as a spur or other marker/spacer, extending radially from sleeve 39 distal end 41 but designed to enter at the opening 14 can also be employed.

In some embodiments, methods include utilizing a coaxial endoscope located near the distal tip for viewing the trabecular meshwork 9 and resultant positioning distal end 41 of probe 23. An endoscope can also be used through a separate self-sealing incision. In some methods, an ultrasound detector or scanner can provide a graphical representation of the tissue anatomy and position of distal end 41 of probe 23 to allow locating the distal end with precision relative to Schlemm's canal, as in A-scan ultrasonograph or ultrasonic biomicroscopy. Ultrasonic biomicroscopy is a technique in which high frequency ultrasound (from about 40-100 MHz) can be used to produce high resolution (about 20 µm) images of biological structures. The structures of interest will generally be located within 4 mm of the surface of the body, or be accessible by an endoscope, because of reduced penetration of ultrasound at these higher frequencies. Regardless of technique used, a landmark, such as Schwalbe's line, is identified. Next, the energy distribution of a selected probe tip 47 is identified. The probe 23 is then applied to the identified landmark so that photoablative energy can be applied from probe tip 47 in a manner applicable to the target tissues.

At step 211, the intraocular pressure can also be monitored by pressure sensor 83 at distal end 41 or at an intraocular portion of the probe 23. Alternatively, an external pressure sensor or transducer can be used to monitor the internal pressure in the stabilized anterior chamber within desired limits. At step 213, the control switches can be operated by the surgeon to arm the laser for firing into the target site. Optionally, as shown in step 215, the trabecular meshwork 9 can be compressed or flattened to an average thickness of about 90 µm to reduce the amount of laser radiation and increase treatment rate. Compression of the meshwork reduces the distance of penetration through the trabecular meshwork from approximately 150 µm to about 90 µm, before the distal end 41 of probe 23 reaches Schlemm's canal. Because each light pulse ablates about 1 or 2 µm of tissue when using a 308 nm excimer laser, the time and number of pulses used for micropenetration is shortened and precision is increased. Compaction can also help to physically stabilize the meshwork. When the meshwork is compacted, the number of pulses needed for penetration can range from about 10 to about 100 pulses, when using ultraviolet wavelengths. In contrast, in the infrared wavelengths, from about 1 to about 20 pulses are typically sufficient to penetrate through the meshwork into Schlemm's canal.

With reference to step 215, a number of approaches can be used to compress the trabecular meshwork at the target site. For example, one approach, shown in FIG. 9, includes physically contacting and applying an axial force so that the distal end of probe 23 being blunted pushes against the meshwork. Tissue contact sensor 73 can provide appropriate notification of the tissue-contact of probe 23. During the advance of the probe into the meshwork, the surgeon can physically view the compaction of the meshwork using the previously described ultrasound scanner, endoscope, or other viewing systems of the eye anatomy.

In some approaches, a viscoelastic fluid of a selected viscosity and molecular size can be used to flatten the trabecular meshwork. Incremental or stepped pressure induced within the eye can be achieved by injecting the viscoelastic fluid from irrigation control 55 by control switches or buttons disposed in handset 25. When using a viscoelastic fluid, the surgeon can slowly increase the pressure until the meshwork compresses to a desired thickness. It should be recognized that servo device 27 can also be employed to increase the pressure automatically by feedback of pressure sensor 83 in the manner shown in FIG. 10.

Whether or not the meshwork is compressed, as shown in step 217, laser unit 31 transmits laser energy via fiber-optic probe 23 so as to photoablate the juxtacanalicular trabecular meshwork and inner wall of Schlemm's canal in the vicinity of the target site. Optionally, concurrent with activation of the laser (see step 217), the irrigation fluid and/or viscoelastic fluid can be supplied into target site of laser energy application. Also, as shown in step 219, while photoablative laser energy is applied to the target site, irrigation fluid and/or vaporized gases can be aspirated in the region of light energy impingement via the aspiration flow path 51 in fiber-optic probe 23. The operation of aspiration control 57 and associated flow path has been previously described. In some embodiments, advantage is taken of the evolved gases to confirm patency of channels formed in the network, as will be described below.

As an alternative to irrigation fluid, therapeutic agents can be izjected into the anterior eye chamber or into Schlemm's canal at or about the same time as photoablation is being performed to help minimize traumatic effects and inhibit self-sealing tendencies of the eye anatomy. In addition to, or separately from, anti-inflammatory agent both steroidal and non-steroidal anti-fibroblastic agents and anti-angiogenic agents, singly or in combination can also be provided. The concurrent application of therapeutic agents advantageously increases the long term benefits of opening the meshwork and Schlemm's canal. It should be recognized that once an opening is created in Schlemm's canal from the fiber-optic probe, the therapeutic agents can be injected into the opening. Specific examples of these types of agents include DFU, which is a nonsteroidal anti-inflammatory, anecortave acetate which is one of the angiostatic steroids, and anti-TGF which is a monoclonal antibody known to inhibit the activity of all three forms of TGF-β. in vivo.

Optionally, as shown in step 221, the distal tip 41 of probe 23 can be advanced inwardly during the photoablation of the tissues and, if the meshwork was flattened, there can be relative movement as the meshwork expands around the aperture. Any resultant relative movement can be measured at step 221 and the results of the measurement can provided in a feedback loop to handset 25 to be used to control further movement of the probe 23. A pilot opening can be created into Schlemm's canal. Agents then can be injected into Schlemm's canal causing it to expand, such that subsequent openings will be less likely to injure the outer wall. More specifically, in order to protect the outer wall of Schlemm's canal, which generally one will not want to puncture, a pilot hole can be created, and Schlemm's canal inflated. The pilot hole can be stented, creating a barrier. A device known as a trabeculatome can be used as such a barrier. The pilot hole can be created and the and stent inserted from a site internal or external to the eye.

While a skilled surgeon can operate fiber-optic probe 23 to penetrate only the proximal inner wall of Schlemm's canal, once in the canal, in some methods the distal outer wall will not be penetrated. Creating a passageway into Schlemm's canal should be of a controlled depth, because penetration too great a depth could be more traumatic to a patient, due to contact with or breaching of the distal wall of the canal.

Optionally, as shown in step 223, detection of penetration of the proximal inner wall of Schlemm's canal can be accomplished in a number of approaches. In some cases, optical methods such as transillumination can be used. In some cases, some methods include viewing an ultrasound scanned image of the target site from an above plan view orientation, for example, using high frequency ultrasound. In some methods to detect penetration of the proximal inner wall, a chemical or photochemical detection method can be used. In these cases, for example, use of a hemoglobin detector is useful to determine whether blood flow has been encountered in Schlemm's canal. This type of method can be performed, for example, by optical spectroscopy of oxygenated and deoxygenated hemoglobin, using diffused light from red diode absorption (e.g., pulse oxymetry). In some embodiments, a sensor method, for example, optical spectroscopy detecting fluorescence by illuminating and detecting substances directly or by fluorescent stimulation, can be used to detect the presence of a marker substance (e.g. a fluorescing dye), which can be added, for example, to a viscoelastic material injected into Schlemm's canal. Examples of such marker substances include, without limitation, fluorescein, indocyanine green or trypan blue. In some embodiments, tissue recognition guidance circuitry of laser delivery system 21 can be used.

Figure 1:
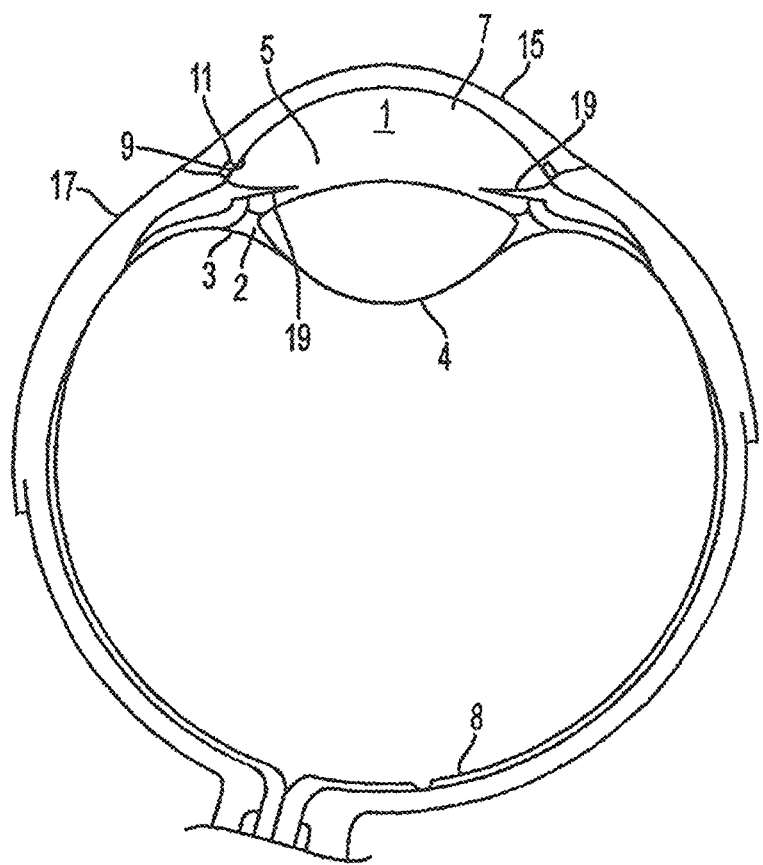
FIG. 1 is schematic sectional view of an eye illustrating the interior anatomical structure.
Figure 2:
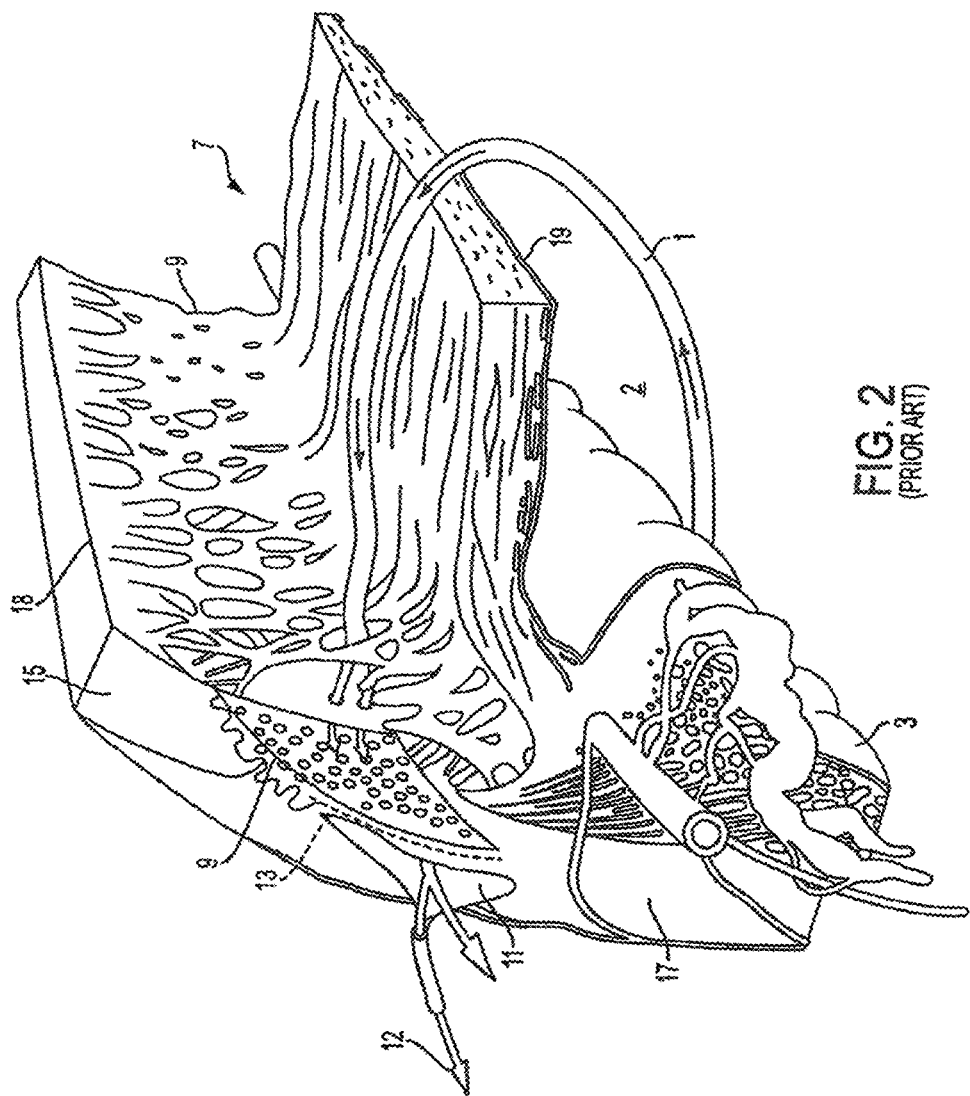
FIG. 2 is a perspective fragmentary view of the anatomy within the anterior chamber of an eye depicting the corneoscleral angle.

As shown in step 225, once penetration of the proximal wall has been detected, the probe 23 can be withdrawn before the distal wall is penetrated. In step 227, probe 23 can be repositioned at an accessible new target site for repetition of the sequence. The probe can subsequently be moved transocularly to a number of different angular locations about the corneoscleral angle, as shown in FIG. 2, in order to create additional radial passages in the periphery of the eye, as previously described. As a result, an adequate number of radial outflow apertures, in some embodiments ranging from two to ten, can be formed in the juxtacanalicular trabecular meshwork 9 and the proximal inner wall of Schlemm's canal 11. The inner proximal wall of the resultant microsculptured Schlemm's canal can have precisely cut or minimally fused ends of tissue as a result of the process described above. Minimal scarring or shearing of tissue will occur so as to discourage initiation of a significant healing response and to provide for controlling and lowering the intraocular pressure for a longer time as compared with previously used techniques.

Figure 14:
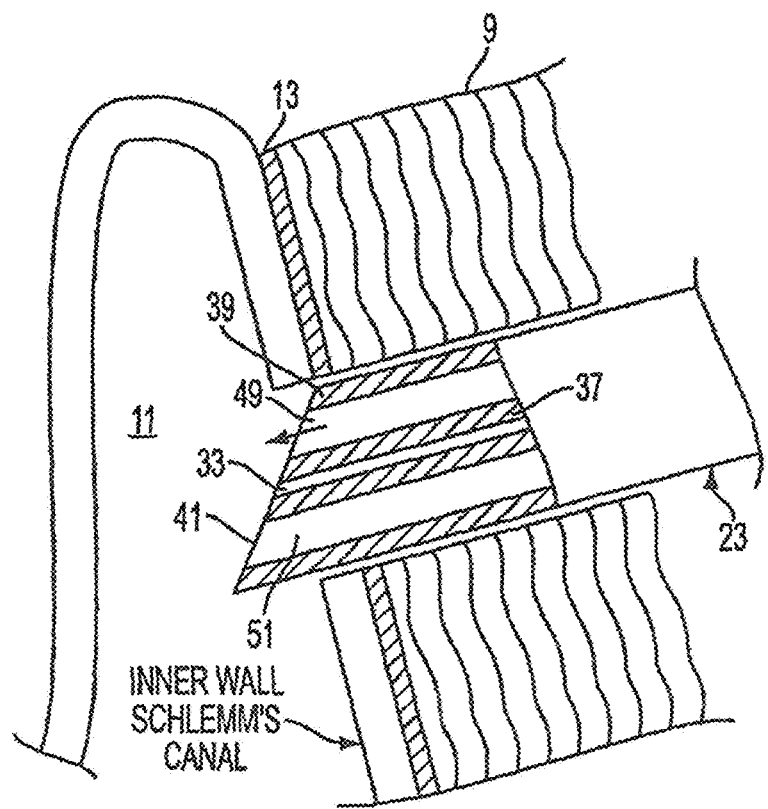
FIG. 14 is a schematic diagram of a an embodiment of a fiber-optic probe for providing fluids/materials into Schlemm's canal.

In some methods, once Schlemm's canal is penetrated, in step 229, for example, as illustrated in FIG. 14, an appropriate viscoelastic fluid can be injected or coaxially infused so as to inflate or expand the canal. Thereafter, once the probe is repositioned to a new target site, a greater margin of error for photoablation exists that reduces the risk of damaging the outer wall. In addition, filling Schlemm's canal with viscoelastic fluid results in a compression of the trabecular meshwork from behind. This compresses the meshwork reducing the thickness of the trabecular meshwork to be ablated and, in addition, separates the inner and outer walls of Schlemm's canal preventing collapse that might occur as a result of the axial compressive force applied by probe 23. In addition, filling Schlemm's canal increases the space between the inner and outer walls to about 300 μm, further reducing the risk of penetrating the outer wall.

It should be recognized that a viscoelastic fluid including therapeutic agents can also be used to expand Schlemm's canal. This can provide multiple benefits, such as, creating a pressure reaction structure, providing a larger target site to photoablation, preventing penetration of the distal wall of Schlemm's canal, and applying therapeutic agents to all openings or perforations in a generally uniform manner. It should be recognized that, once performed, expansion of Schlemm's canal will usually not have to be repeated, but can be if indicated. In some methods, once Schlemm's canal is penetrated, a device such as a tube, stent or viscoelastic material can be positioned in the passage into Schlemm's canal to prevent injury to its outer wall. This device can also be introduced into Schlemm's canal from outside of the eye via a separate incision.

Figure 15:
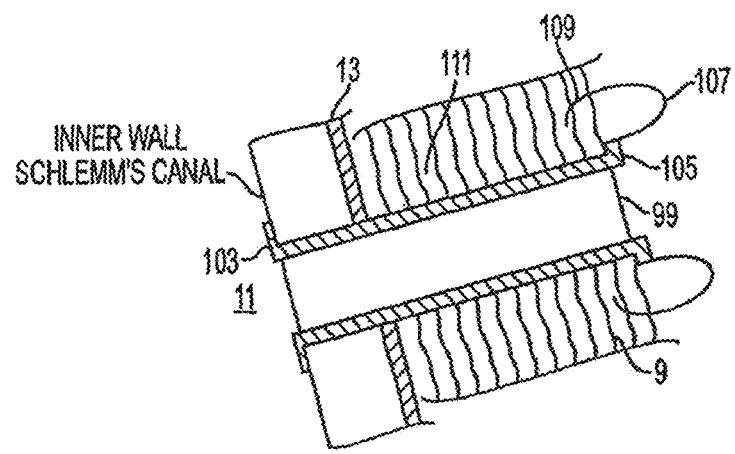
FIG. 15 is a schematic diagram of an embodiment of an intraocular intracannalicular implant device.

Referring now to FIGS. 15-18B, devices and a technique are shown for controlling the geometry of Schlemm's canal 11 and optionally the trabecular meshwork 9. Referring to FIG. 15, an intraocular implant device 99 is illustrated. Implant device 99 self-retains in the inner wall of Schlemm's canal 11 and can extend into and through the trabecular meshwork 9. Implant device 99 can be embodied in a stent having an elongated tubular body 101. Implant device 99 can include a valve leaflet to ensure unidirectional outflow. The distal end of tubular body 101 can include a plurality of foldable legs 103 for engaging the inner wall of Schlemm's canal when they are fully deployed. The proximal end of tubular body 101 includes a flange portion 105 and a plurality of thin elongated cylindrical projections 107 having hook-like distal ends 109 for linking or hooking into the trabecular meshwork 9.

Figure 16:
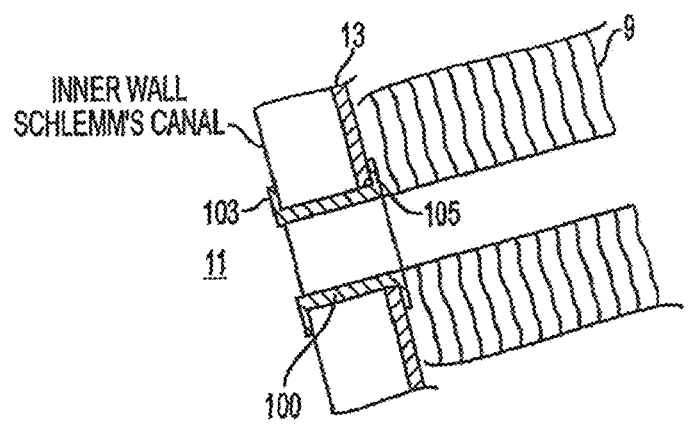
FIG. 16 is a schematic diagram of an embodiment of an intraocular intracannalicular implant device.

Tubular body 101 can have an inner diameter dimension of about 10-200 μm and an outer diameter of less than about 1000 μm. Foldable legs 103 typically can be in a range from about 5 μm to about 50 μm. Cylindrical projections 107 can have dimensions in a range from about 5 µm to about 50 µm, and can appear similar to hooks of Velcro, which self-engage and self-retain. Implant device 99 can be constructed from a biocompatible, inert material capable of being sterilized and unlikely to stimulate a foreign body reaction. Tubular body 101 can be constructed from materials such as, for example, and without being limiting, thermoplastic, stainless steel, PMMA, nylon or polypropylene. Foldable legs 103 and cylindrical projections 107 can be made from one of these same or other materials. With reference to FIG. 16, an alternative implant device 100 is illustrated. Device 100 can be similar to the structure of device 99. In some embodiments, the tubular body extends only about the thickness of the inner wall of Schlemm's canal.

Figure 17:
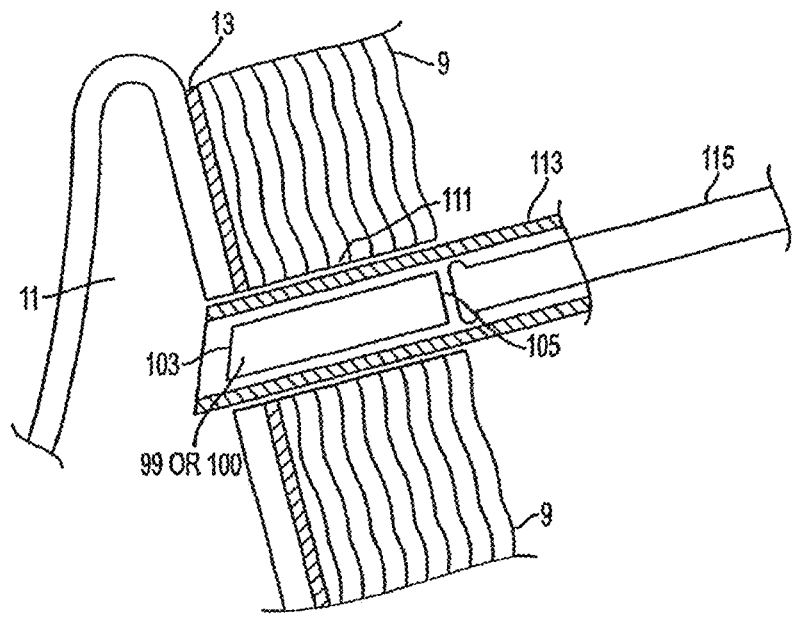
FIG. 17 is a fragmentary schematic diagram of a system for implanting devices like those depicted in FIGS. 15 and 16 into the eye.

An exemplary embodiment of a system and method of positioning the implant device is illustrated in FIG. 17. A self-sealing opening is created in the cornea of the eye. A cutting cannula or fiber-optic probe 23 can be inserted and advanced transocularly through the anterior chamber to open a cylindrical aperture 111 extending from trabecular meshwork 9 to Schlemm's canal 11. This cannula or the probe can then be withdrawn from the eye. Implant device 99 can be retained or carried inside a distal end of an inserter device 113. Such configurations enable a distal end of an implant device 99 having foldable legs 103 to be positioned for eventual implantation into aperture 111 and Schlemm's canal 11. The proximal end of implant device 99 abuts a central shaft or plunger member 115. Central shaft 115 can be slidably engaged within inserted tube 113. Next, the distal end of inserter tube 113 having implant device 99 is introduced through the opening and advanced to cylindrical aperture 111. Thereafter, the surgeon can position the distal end of inserter tube 113 such that implant device 99 is inserted into the aperture.

Figure 18A:
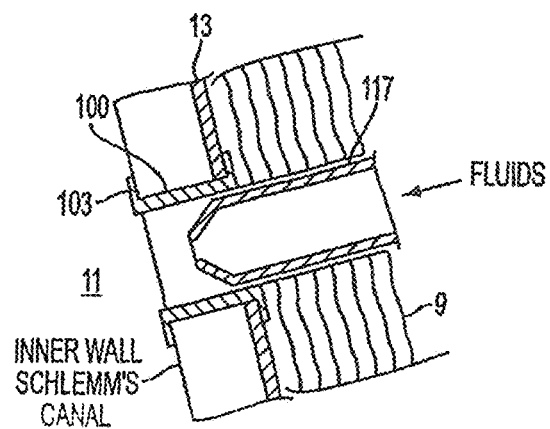
FIGS. 18A-18B are schematic diagrams of an embodiment of a system providing fluids/materials in Schlemm's canal.
Figure 18B:
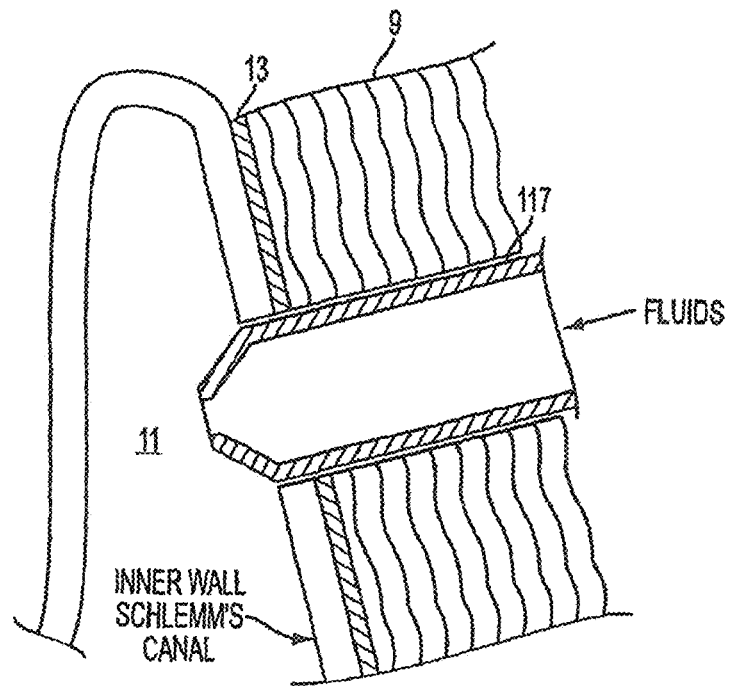

Once the implant device is in the aperture 111, central shaft 115 can be advanced forward to push the distal end of implant device 99 into and through the inner wall of Schlemm's canal 11. Foldable legs 103 can then be unrestrained and released into the proximal inner wall of Schlemm's canal 11. The inserter tube and central shaft are withdrawn from the aperture. At this point the cylindrical projections of the proximal end of implant device engage the trabecular meshwork 9. If desired, as shown in FIG. 18A, a feeder tube 117 can abut within the proximal opening of the tubular body and various therapeutic agents or viscoelastic fluids can be provided into the canal. In some embodiments, as shown in FIG. 18B, an implant device can be eliminated and feeder tube 117 can be inserted into Schlemm's canal 11 to inject fluids. Nevertheless, it should be recognized that an implant device can be inserted into each aperture that has been formed in the trabecular meshwork 9. In some embodiments, a grommet unit can be used in place of a stent. In some embodiments, grommets or stents can further include a one way valve. In some embodiments, the inserter device can be configured with circuitry similar to fiber-optic probe 23. For example, distal end of inserted tube 113 can include a tissue-contact sensor to detect when the meshwork is contacted by tube 113.

The system and method of treatment for glaucoma can be adapted to account for variations in the relative position and character of Schlemm's canal as well as anatomical differences in the trabecular meshwork from patient to patient. It will be recognized that other alternatives can present themselves to those skilled in the art. Fabrication techniques used for miniaturized devices can be employed to form sensors, actuators and conductors on the inserted portion of a probe. Probes can be designed so that it is disposable wholly or in major part. The tip end of the probe can be angled to or deflect off a small mirror or prism according to the angle of the trabecular meshwork. A variety of other types of irrigation and aspiration can be used with the probe to perform the function described. For example, and without being limiting, irrigation fluid can be fed in between the outside of the metal sleeve and the inner surface of a concentric shield that conforms to and seals the incision or via a separate incision.

In some embodiments, advantage is taken of the fact that, during excimer laser trabeculostomy (ELT), gases are evolved as a result of the photoablation process. Devices for performing ELT are described in U.S. Pat. No. 4,846,172, and U.S. patent application Ser. No. 09/860,842, the contents of which are herein incorporated by reference.

During an ELT procedure, a probe emitting photoablative energy, for example, via a fiber-optic delivery system can be configured such that gas escaping from tissue wells created by the photoablation process can be monitored and/or characterized. The probe can include, or be coupled to, high resolution imaging apparatus, for example optical coherence tomography via the sclera, via the cornea with a goniolens, and ab interno via a optical fiber. In some embodiments, the probe can be configured to introduce a viscoelastic fluid into the surgical site. In some embodiments, a separate source of viscoelastic fluid can be provided. In some embodiments, the gas resulting from photoablation can be trapped as bubbles both in the tissue wells being created, and in the viscoelastic and/or aqueous humor that fill the wells, and which fills the anterior chamber and maintains the anterior chamber depth. During the procedure, the trabecular meshwork thickness can be compressed, maintained, or otherwise altered, for example, by adjusting the amount and/or pressure of viscoelastic material placed in the anterior chamber.

As the tissue is transformed at the leading edge of the fiber-optic delivery system, evolved gases formed are expelled, and accrete as visible bubbles around the probe. As the wells become deeper, and so long as there is resistance to outflow of both fluid and the evolved gases, gas will be expelled retrograde, in the direction of the anterior chamber. Advantageously, in some embodiments, the apparatus can be configured such that during photoablation, as soon as the resistance is overcome by perforation of the juxtacanalicular trabecular meshwork and the inner wall of Schlemm's canal, the evolving gases will be directed inwards into a space behind the tissue being ablated. For example, in the eye, the space behind the trabecular meshwork would include the lumen of Schlemm's canal.

Figure 22:
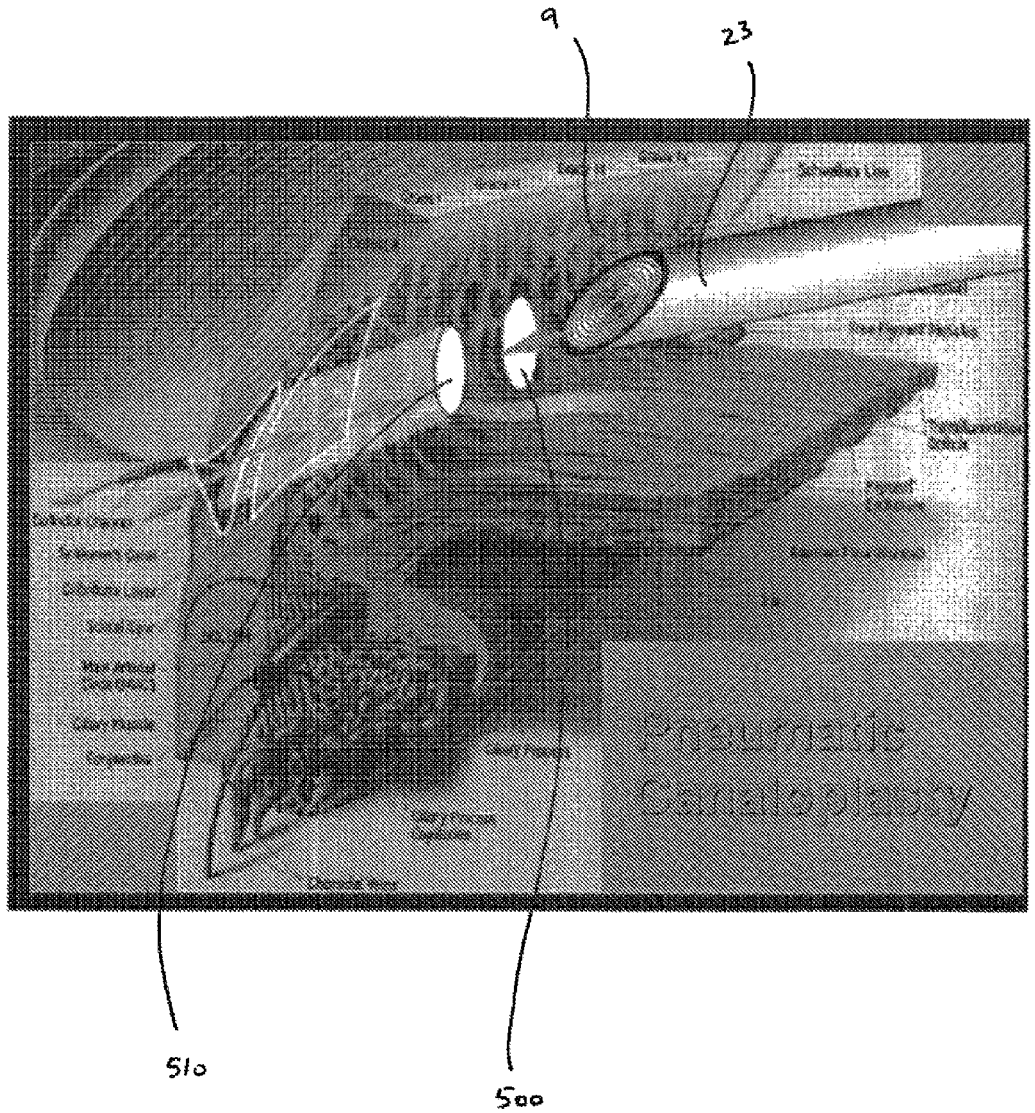
FIG. 22 illustrates an embodiment of a pneumatic canaloplasty procedure.
Figure 23:
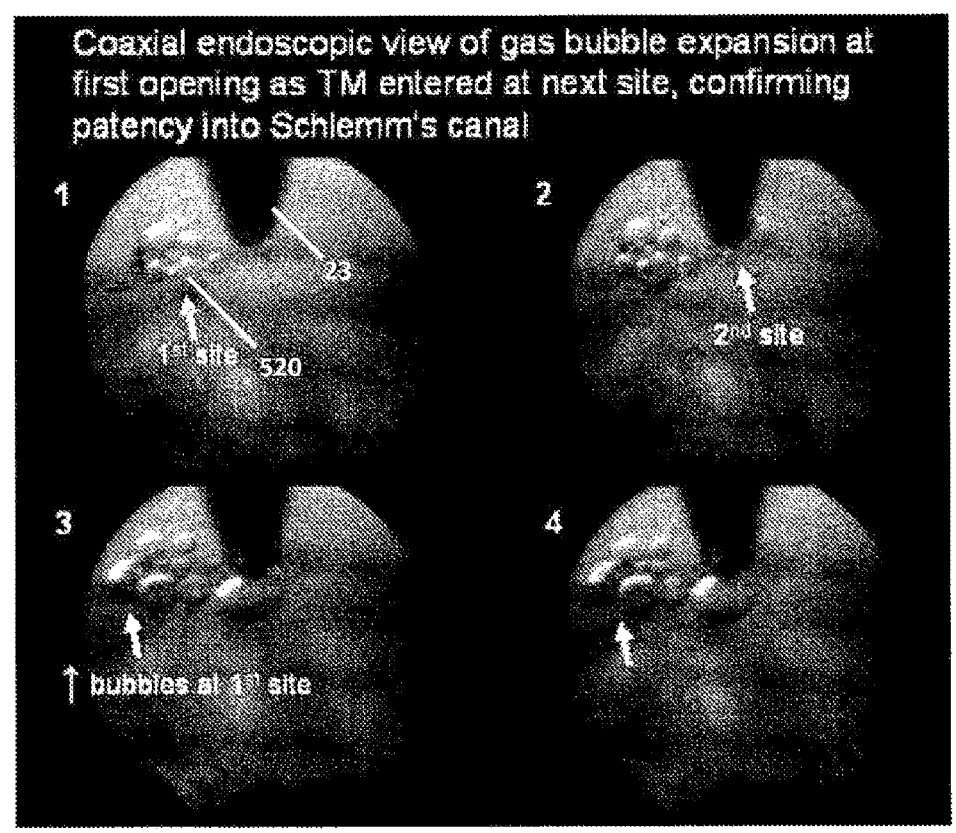
FIG. 23 shows results of a canaloplasty procedure where bubbles generated at a second treatment site appear at an aperture formed at a first treatment site.

Therefore, for example and without being limiting, as gas evolves into Schlemm's canal, the pressure in the canal will increase. This increase in pressure is effective to dilate both the canal, and confluent connector channels. In some embodiments, the probe is configured to selectively overcome this resistance. Where a procedure involves making multiple perforations through the trabecular meshwork, gas bubbles 520 formed by photoablation at a second location 500, can be observed unexpectedly to escape Schlemm's back into the anterior chamber of the eye through an aperture formed previously at a first location 510, as shown in FIGS. 22 and 23. Thus, one can both confirm the patency of apertures formed at prior treatment sites, as well as to confirm the formation of subsequent apertures, since until the probe has formed a passage that completely crosses the trabecular meshwork, evolved gases will be evolved into Schlemm's canal, from which they can escape via previously formed passages.

In some embodiments, the photoablative process, the environment surrounding the site of photoablation, and the photoablation probe, can each be configured to control the size of the gas bubbles that will be evolved during ablation. In addition, the rate of bubble formation, and expansion and directionality of bubbles as gas is produced, can also be monitored and modulated. Conveniently, a probe 23 can be configured to monitor the local and regional tissue effects, and provide feedback with which to control the parameters described above. Control can be effected by monitoring one or more of the tissue, pressures and densities of the tissue being ablated and the surrounding tissue, temperature of the tissue being ablated and the surrounding tissue, as well as laser parameters, for example, pulse duration, repetition rate, and photon density. The distribution can depend on the cleavage planes, the delivery system, and other means of controlling gas distribution, both physical and structural.

In some embodiments, the photoablation system comprises at least one sensor, configured to detect at least one of contact with the tissue to be ablated, and the formation of evolved gas in the form of bubbles in the space behind the tissue being ablated. Detecting contact can be accomplished by sensors that are configured changes in a force applied to the end of a photoablative probe, as described above, or other members on the device, or by sensing changes in parameters such as capacitance as will occur when the photoablation probe, or a sensing member, comes into intimate contact with the surface of the tissue to be ablated, for example the trabecular meshwork.

In some embodiments, the photoablation laser can further include a sensor configured to detect the formation of bubbles in the space behind the tissue being ablated. This could include, for example, providing imaging capability in the form of a camera that acquire images while photoablation is being performed. The imaging system can further include software or other capabilities adapted to detect bubble formation and/or the presence of bubbles arising from an aperture. The sensing system can also be adapted to display the images on a monitor or other display device for the convenience of the surgeon.

Dilating Schlemm's canal can be effective to lower intraocular pressure, for example, using the viscocanalostomy or canalostomy surgical techniques. Surgical intervention methods, however, required ab externo surgical incisions as well as the injection of liquids or viscoelastic fluids.

In contrast, embodiments as described herein make use of the gas evolved during photoablation as a dilating agent. Dilating Schlemm's canal not only enables a larger volume of flow, but also impacts on structures within Schlemm's canal to further increase outflow. For example, dilation stretches and alters the mobility of the trabecular meshwork and the Schlemm's canal membrane, structures that in open angle glaucoma can become partially obstructed and less mobile. Thus, in some embodiments, resistance to outflow can be reduced by creating openings in the trabecular meshwork and inner wall of Schlemm's canal. In addition, intraocular pressure can be reduced by dilating Schlemm's canal and collector channels, further enhancing outflow.

In some embodiments, conditions are optimized to favor pneumatic canaloplasty/tissueplasty as part of a photoablative laser system and method. In some embodiments, the process of photoablation is practiced in a closed environment, such that when released, the products of ablation (e.g., evolved gases) result in an increase in pressure in the surrounding enclosed volume. This is in contrast to surface photoablation processes, for example, photoablation of the cornea, where ablation products are expelled into the atmosphere.

In an ELT procedure, therefore, ablation products are initially liberated into the closed environment surrounding the trabecular meshwork. Once the meshwork has been penetrated, the orientation of the laser probe is configured such that the products evolve into Schlemm's canal. Schlemm's canal is also under pressure from the fluid within it, as well as from pressure exerted by the intraocular pressure and viscoelastic components of the anterior chamber. These combine to compress the trabecular meshwork and Schlemm's canal, all of which contributes to the closed environment, where gas released during photoablation can affect structural changes in the vicinity of the volume into which the gas is released.

Figure 24:
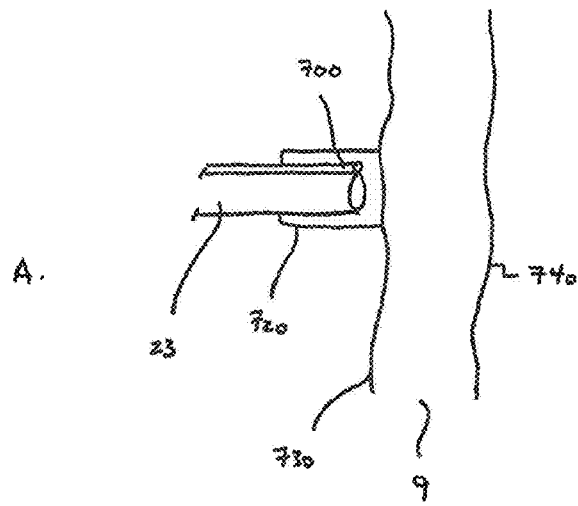
FIG. 24A-24C depicts embodiments of pneumatic tissueplasty as described herein.
Figure 24:
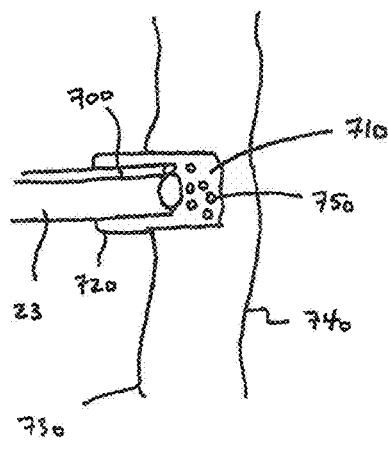
Figure 24:
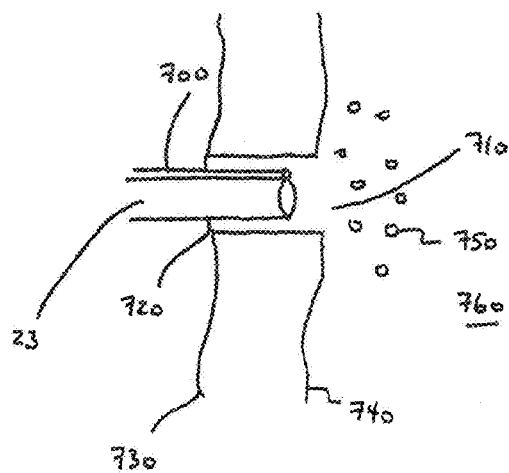

In some embodiments, as illustrated in FIG. 24, a probe 23 can include a gas injector module 700. In these embodiments, pressurized gas from an external supply can be fed through the gas injector module 700, into an aperture 710 formed by the photoablative action of the probe 23. The gas injector module can be configured to augment the population of bubbles formed as a result of the photoablation procedure and to provide further capacity for inflation of a space lying distal to the site of application of a photoablation treatment. For example, in some embodiments, the external gas supply can be used to inflate at least a portion of the lumen of Schlemm's canal to improve flow.

In some embodiments, a probe 23 can also include a hood 720, configured to make contact with a proximal surface 730 of a tissue to be photoablated. The hood 720 is also effective to direct gas bubbles 750 evolved during photoablation into the aperture 710 formed by the photoablation process, also shown in FIG. 24. As described above, the beam width can be configured such that an aperture of approximately the same diameter as the probe is created. Thus, as the aperture forms, the probe 23 and hood 720 can be advanced into the aperture 710 such that gas bubbles are directed almost entirely into the aperture, as shown in FIG. 24 B.

Once an aperture 710 has been formed that traverses the width of the tissue, as shown in FIG. 24C, the hood and probe can cooperate to direct the gas bubbles 750 into the space 760 adjacent to the distal surface 740 of the tissue being treated. In some embodiments, the probe 23 is configured without a hood, and the probe 23 is effective to direct gas bubbles 750 formed by photoablation through the aperture. The gas bubbles will tend to cause inflation of the space into which they are directed, for example, a portion of the lumen of Schlemm's canal. In addition, as described above, gas bubbles directed into the distal space can re-emerge through a previously formed aperture, thus confirming the patency of both a first and second apertures formed in a tissue layer.

In addition to use in dilating Schlemm's canal in the eye, the apparatus and methods described herein can also be used to dilate other structures in the body. These can include, for example and without limitation, arteries, veins, lymph nodes, to move membranes, as in vitreous, retina, all cartilage surfaces, as in nose, throat, knee, shoulder, hip, and in other tissues where adhesions can occur or separation of matter is desired, such as prostate, joint spaces, spinal disc etc. Thus, the described apparatus and methods can be used in connection with applications other than glaucoma treatment, and anywhere that photoablative energy can be delivered. This can include any endoscopic surgeries in which photoablation is used to remove tissue or separate tissues (e.g., arthroscopy, prostate, breast, cardiac, etc.). Another example of use includes the generation or introduction of gases intrathecally, to move, alter, and/or separate structures or tissue.

While the ELT procedure provides a way of introducing gas into closed channels for the purpose of altering structures and/or tissue, the ELT procedure is not required for treatment by introduction of gases. For example, gases or aerosols can be introduced into or near the treated tissue without the need for tissue ablation. In such applications, pressurized gas is introduced into the TM, SC, collector channels, and/or other natural outflow channels or pathways to move, alter, and/or separate structures or tissue. While the procedures described above and depicted in the accompanying drawings depict ab interno applications, ab externo procedures can also be used in connection with the subject matter disclosed herein.

Treatment of tissue by introduction of gases can be enhanced by utilizing the gas as a carrier for therapeutic and/or biological agents. For example, medications can be co-administered with a gas in the form of an aerosol, or mist, into the trabecular meshwork, Schlemm's canal or other ocular structures, channels, or paths in order to enhance healing, inhibit inflammation or to modulate vascularization, for example. Examples can include steroids, immunomodulators, genes, proteins, and antiglaucoma agents.

In some embodiments, the method can include pressing the tip photoablative probe up against the trabecular meshwork. This can aid in directing evolved gas into the lumen of Schlemm's canal once the meshwork has been penetrated by the photoablative energy. In some embodiments, the margins of the aperture produced during photoablation stretches, and is able to slide over the circumference of the ablation tip, providing an improved seal of the tip in the forming aperture. Where a plurality of apertures are to be formed in the trabecular meshwork, the present methods and apparatus provide an advantage both in confirming the patency of previously formed apertures (by the appearance of bubbles from within the interior of Schlemm's canal) as well as to confirm the penetration of the trabecular meshwork and the wall of Schlemm's canal at the site being treated.

Figure 25:
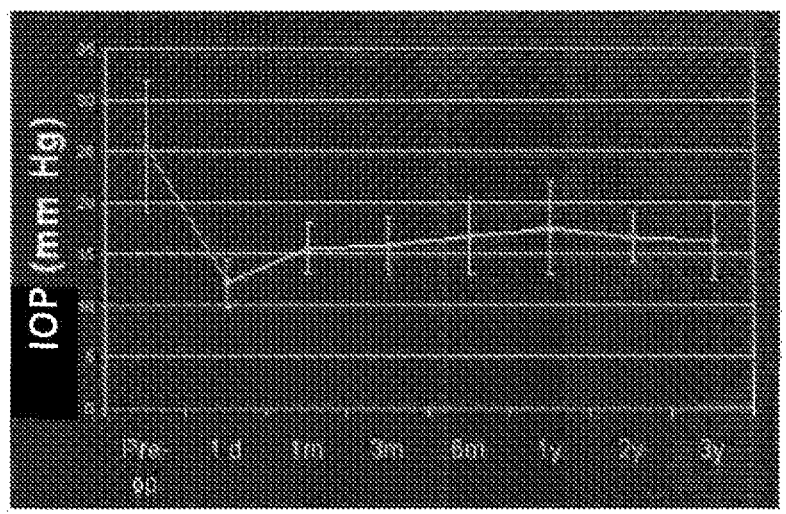
FIG. 25A-25B illustrates results from two studies showing the long-term effectiveness of canaloplasty at lowering intraocular pressure in patients.
Figure 25:
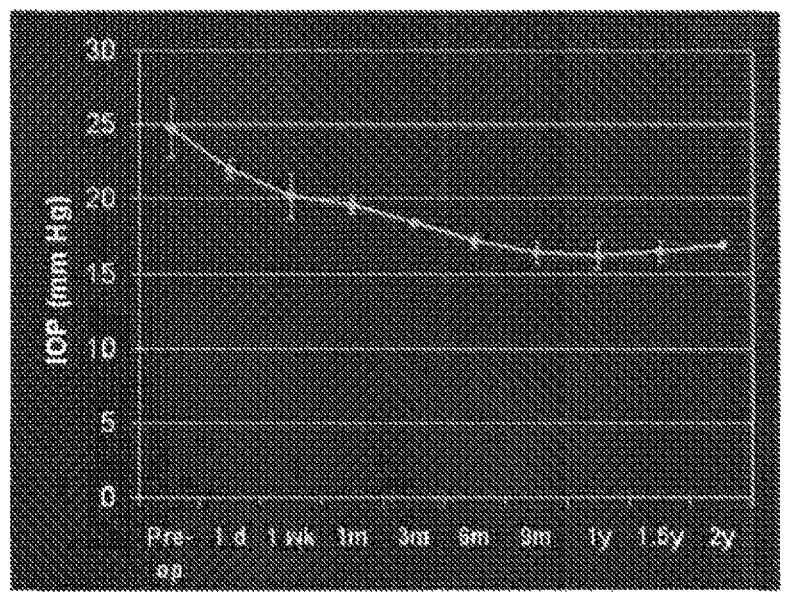
Figure 26:
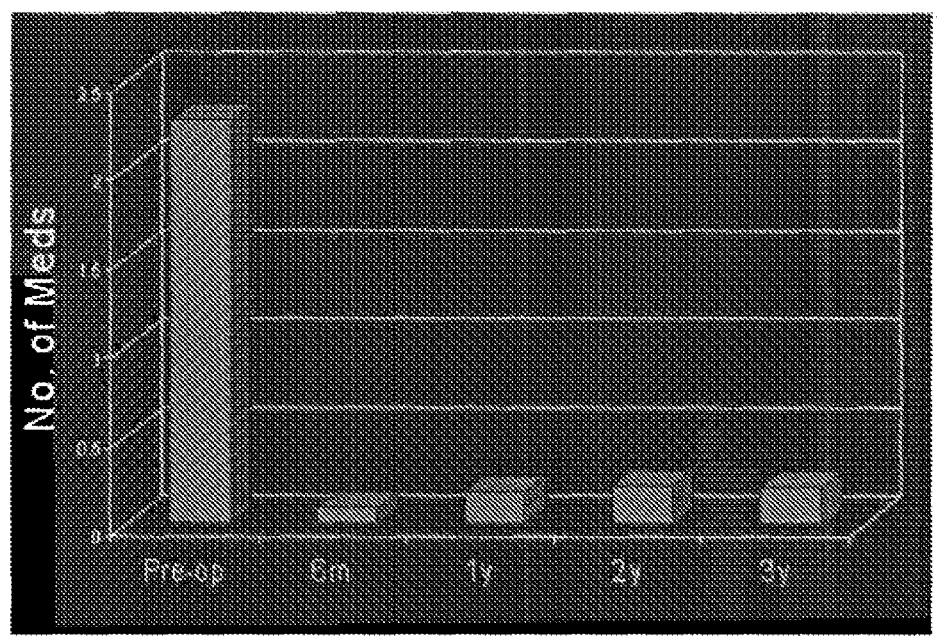
FIG. 26 illustrates the effectiveness of an exemplary canaloplasty procedure in reducing the number of medications required for patients to maintain reduced intraocular pressure.

In treating glaucoma, embodiments of the apparatus and methods described are effective lower intraocular pressure (IOP) immediately after surgery and to maintain lower pressure over extended periods of time. For example, as shown in FIGS. 25A and B, results from two separate studies showed that pneumatic tissueplasty resulted in a reduction in average IOP from about 25 mmHg to between about 13 Hg and about 16 Hg. In both studies, pressures below 17 mmHg were maintained for at least three years following surgery. Normal IOP generally ranges from about 10-20 mmHg, with a diurnal variation of between 3-6 mmHg. In addition, the number of medications taken by patients as glaucoma control aids could be reduced following surgery. As shown in FIG. 26, preoperatively, the need for pharmaceutical aids to maintain lower pressure was also significantly reduced. In addition, of patients treated, more than 50% were able to achieve 20% or greater reduction in IOP without the need of any additional medication.

While this disclosure has been described with reference to preferred embodiments, it will be understood by those skilled in the art that various changes can be made and equivalents can be substituted for elements thereof without departing from the scope of the invention. In addition, many modifications can be made to adapt a particular situation or material to the teachings of the invention without departing from the scope thereof. For example, a micro drill can be used employed instead of a fiber-optic probe to penetrate the trabecular meshwork and Schlemm's canal.

Also it should be recognized that the concept of compressing the eye anatomy with viscoelastic material is applicable to other tissues such as joint cartilage, ligaments, arachnoid tissue and the like and fiber-optically introduced photoablation of these tissues to effect pressure control and tissues removal for alterations of tissue structure, fluid flow and placement of devices such as stents or anchors. The techniques described in the present invention can be used as an adjunct to current endoscopic surgical procedures. More specifically, tissues can be identified endoscopically and photo ablated as previously described according to the present invention. Therefore, it is intended that the invention not be limited to the particular embodiment disclosed, but that the invention will include all embodiments falling within the scope of the appended claims.

The skilled artisan will recognize the interchangeability of various features from different embodiments. Similarly, the various features and steps discussed above, as well as other known equivalents for each such feature or step, can be mixed and matched by one of ordinary skill in this art to perform compositions or methods in accordance with principles described herein. Although the disclosure has been provided in the context of certain embodiments and examples, it will be understood by those skilled in the art that the disclosure extends beyond the specifically described embodiments to other alternative embodiments and/or uses and obvious modifications and equivalents thereof. Accordingly, the disclosure is not intended to be limited by the specific disclosures of embodiments herein.

What is claimed is:

1. A method, for treating glaucoma in an eye, the eye comprising an anterior chamber, a Schlemm's canal and a trabecular meshwork therebetween, the method comprising:
    photoablating ocular tissue at a first treatment site, resulting in the formation of a first aperture in the ocular tissue, the first aperture extending from the anterior chamber through the trabecular meshwork into the Schlemm's canal; and
    photoablating the ocular tissue at a second treatment site, resulting in the formation of a second aperture in the ocular tissue, the second aperture extending from the anterior chamber through the trabecular meshwork into the Schlemm's canal;
    wherein photoablating the ocular tissue at the second treatment site generates a pressurized gas that travels along the Schlemm's canal toward the first aperture.

2. The method of claim 1, wherein the Schlemm's canal is dilated with the pressurized gas between the first aperture and the second aperture.

3. The method of claim 1, wherein the pressurized gas from the second treatment site travels along the Schlemm's canal to the first aperture.

4. The method of claim 1, wherein the photoablating of the ocular tissue at the second treatment site is performed in an enclosed volume of the eye and the pressurized gas provides an increase in pressure within the enclosed volume.

5. The method of claim 1, wherein the Schlemm's canal is dilated with the pressurized gas and dilation of the Schlemm's canal allows a larger volume of flow through the Schlemm's canal, thereby increasing outflow.

6. The method of claim 1, wherein treatment comprises the photoablating ocular tissue at the first treatment site and the photoablating ocular tissue at the second treatment site and wherein an intraocular pressure of the eye is decreased by 20% or more after the treatment as compared to before the treatment.

7. The method of claim 1, wherein the pressurized gas provides dilation of confluent connector channels in the eye.

8. The method of claim 1, comprising: controlling the pressurized gas generation, by controlling at least one of: (1) process parameters applied during the photoablating of the ocular tissue at each of the first and second treatment sites, (2) an environment surrounding each of the first and second treatment sites, or (3) a size of a photoablation probe that is used for the photoablating of the ocular tissue at the each of the first and second treatment sites.

9. The method of claim 8, wherein the pressurized gas generation forms a gas bubble and wherein the controlling of the pressurized gas generation comprises controlling at least one of: (1) a size of the gas bubble, (2) a rate of gas bubble formation, (3) expansion of the gas bubble, or (4) directionality of movement of the gas bubble within and along the Schlemm's canal.

10. The method of claim 8, wherein the process parameters comprise a pulse duration, repetition rate, and/or photon density of a laser that is used for the photoablating of the ocular tissue at each of the first and second treatment sites.

11. The method of claim 1, wherein a number of apertures formed in the ocular tissue between the anterior chamber and the Schlemm's canal is more than two, the number of apertures including the first aperture and the second aperture.

12. A method, for treating glaucoma in an eye, the eye comprising an anterior chamber, a Schlemm's canal and a trabecular meshwork therebetween, the method comprising:
photoablating ocular tissue at a first treatment site, resulting in the formation of a first aperture in the ocular tissue, the first aperture extending from the anterior chamber through the trabecular meshwork into the Schlemm's canal; and
photoablating the ocular tissue at a second treatment site, resulting in the formation of a second aperture in the ocular tissue, the second aperture extending from the anterior chamber through the trabecular meshwork into the Schlemm's canal;
wherein photoablating the ocular tissue at the second treatment site generates a gas bubble that travels along the Schlemm's canal toward the first aperture.

13. The method of claim 12, wherein the gas bubble extends along and dilates the Schlemm's canal at a location between the second aperture and the first aperture.

14. The method of claim 12, wherein the Schlemm's canal is dilated with the gas bubble between the first aperture and the second aperture.

15. The method of claim 12, wherein the gas bubble from the second treatment site travels along the Schlemm's canal to the first aperture.

16. The method of claim 12, wherein the photoablating of the ocular tissue at the second treatment site is performed in an enclosed volume of the eye and the gas bubble provides an increase in pressure within the enclosed volume.

17. The method of claim 12, wherein the Schlemm's canal is dilated with the gas bubble and dilation of the Schlemm's canal allows a larger volume of flow through the Schlemm's canal, thereby increasing outflow.

18. The method of claim 12, wherein treatment comprises the photoablating ocular tissue at the first treatment site and the photoablating ocular tissue at the second treatment site and wherein an intraocular pressure of the eye is decreased by 20% or more after the treatment as compared to before the treatment.

19. The method of claim 12, wherein the gas bubble provides dilation of confluent connector channels in the eye.

20. The method of claim 12, comprising: controlling the gas bubble generation by controlling process parameters applied during the photoablating of the ocular tissue at each of the first and second treatment sites, wherein the process parameters comprise a pulse duration, repetition rate, and/or photo density of a laser that is used for the photoablating of the ocular tissue at each of the first and second treatment sites.

21. The method of claim 12, wherein a number of apertures formed in the ocular tissue between the anterior chamber and the Schlemm's canal is more than two, the number of apertures including the first aperture and the second aperture.

* * * * *